(12) United States Patent
Han et al.

(10) Patent No.: US 12,274,294 B2
(45) Date of Patent: Apr. 15, 2025

(54) AEROSOL GENERATING APPARATUS AND CRADLE CAPABLE OF RECEIVING SAME

(71) Applicant: KT&G CORPORATION, Daejeon (KR)

(72) Inventors: Jung Ho Han, Daejeon (KR); Hun Il Lim, Seoul (KR); Jong Sub Lee, Seongnam-si (KR); Dae Nam Han, Daejeon (KR); Jin Young Yoon, Seoul (KR); Young Lea Kim, Seoul (KR); Jang Uk Lee, Seoul (KR); Ji Soo Jang, Seoul (KR); Wang Seop Lim, Anyang-si (KR); Moon Bong Lee, Seoul (KR); Soung Ho Ju, Daejeon (KR); Du Jin Park, Seoul (KR); Seong Won Yoon, Yongin-si (KR)

(73) Assignee: KT&G CORPORATION, Daejeon (KR)

(*) Notice: Subject to any disclaimer, the term of this patent is extended or adjusted under 35 U.S.C. 154(b) by 0 days.

(21) Appl. No.: 16/498,977

(22) PCT Filed: Mar. 29, 2018

(86) PCT No.: PCT/KR2018/003691
§ 371 (c)(1),
(2) Date: Sep. 27, 2019

(87) PCT Pub. No.: WO2018/182322
PCT Pub. Date: Oct. 4, 2018

(65) Prior Publication Data
US 2021/0106051 A1    Apr. 15, 2021

(30) Foreign Application Priority Data

Mar. 30, 2017  (KR) .................. 10-2017-0040787
Apr. 11, 2017  (KR) .................. 10-2017-0046938
(Continued)

(51) Int. Cl.
A24F 40/30    (2020.01)
A24D 1/20     (2020.01)
(Continued)

(52) U.S. Cl.
CPC .............. *A24F 40/30* (2020.01); *A24D 1/20* (2020.01); *A24D 3/061* (2013.01); *A24D 3/17* (2020.01);
(Continued)

(58) Field of Classification Search
None
See application file for complete search history.

(56) References Cited

U.S. PATENT DOCUMENTS 2,638,904 A    4/1950  Mitchell
4,585,014 A    4/1986  Fry
(Continued)

FOREIGN PATENT DOCUMENTS

CA    2 973 143 A1    8/2016
CA    2 975 654 A1    8/2016
(Continued)

OTHER PUBLICATIONS

US 11,089,812 B2, 08/2021, Zuber et al. (withdrawn)
(Continued)

*Primary Examiner* — Katherine A Will
(74) *Attorney, Agent, or Firm* — Sughrue Mion, PLLC

(57) ABSTRACT

Provided are an aerosol generating apparatus including a cigarette insertion portion into which a cigarette is insertable; and a vaporizer configured to heat a liquid composition to generate aerosol and discharge the generated aerosol toward the inserted cigarette such that the generated aerosol
(Continued)

passes through the cigarette inserted into the cigarette insertion portion, and a cradle for receiving the aerosol generating apparatus.

14 Claims, 7 Drawing Sheets

(30) Foreign Application Priority Data

Jun. 19, 2017 (KR) .................. 10-2017-0077586
Nov. 7, 2017 (KR) .................. 10-2017-0147605

(51) Int. Cl.
| | | |
|---|---|---|
| A24D 3/06 | (2006.01) | |
| A24D 3/17 | (2020.01) | |
| A24F 40/10 | (2020.01) | |
| A24F 40/20 | (2020.01) | |
| A24F 40/46 | (2020.01) | |
| A24F 40/50 | (2020.01) | |
| A24F 40/51 | (2020.01) | |
| A24F 40/53 | (2020.01) | |
| A24F 40/57 | (2020.01) | |
| A24F 40/485 | (2020.01) | |

(52) U.S. Cl.
CPC .............. *A24F 40/10* (2020.01); *A24F 40/20* (2020.01); *A24F 40/46* (2020.01); *A24F 40/50* (2020.01); *A24F 40/51* (2020.01); *A24F 40/53* (2020.01); *A24F 40/57* (2020.01); *A24F 40/485* (2020.01)

(56) References Cited

U.S. PATENT DOCUMENTS

| | | |
|---|---|---|
| 4,637,407 A | 1/1987 | Bonanno et al. |
| 5,144,962 A | 9/1992 | Counts et al. |
| 5,240,012 A | 8/1993 | Ehrman et al. |
| 5,249,586 A | 10/1993 | Morgan et al. |
| 5,369,723 A | 11/1994 | Counts et al. |
| 5,388,594 A | 2/1995 | Counts et al. |
| 5,465,738 A | 11/1995 | Rowland |
| 5,479,948 A | 1/1996 | Counts et al. |
| 5,499,636 A | 3/1996 | Baggett, Jr. et al. |
| 5,505,214 A * | 4/1996 | Collins .................. H05B 3/24 131/194 |
| 5,567,286 A | 10/1996 | Pal et al. |
| 5,591,368 A | 1/1997 | Fleischhauer et al. |
| 5,666,977 A | 9/1997 | Higgins et al. |
| 5,666,978 A | 9/1997 | Counts et al. |
| 5,878,752 A | 3/1999 | Adams et al. |
| 5,967,148 A | 10/1999 | Harris et al. |
| 6,040,560 A | 3/2000 | Fleischhauer et al. |
| 6,053,176 A | 4/2000 | Adams et al. |
| 6,418,938 B1 | 7/2002 | Fleischhauer et al. |
| 6,532,965 B1 | 3/2003 | Abhulimen et al. |
| 6,615,840 B1 | 9/2003 | Fournier et al. |
| 6,810,883 B2 | 11/2004 | Felter et al. |
| 7,861,726 B1 | 1/2011 | Lukasavitz |
| 8,375,959 B2 | 2/2013 | Dittrich et al. |
| 8,419,085 B2 | 4/2013 | Kim et al. |
| 8,464,726 B2 | 6/2013 | Sebastian et al. |
| 8,752,545 B2 | 6/2014 | Buchberger |
| 8,851,081 B2 | 10/2014 | Fernando et al. |
| 8,973,587 B2 | 3/2015 | Liu |
| 9,078,472 B2 | 7/2015 | Liu |
| 9,078,473 B2 | 7/2015 | Worm et al. |
| 9,115,471 B2 | 8/2015 | Zitturi et al. |
| 9,220,304 B2 | 12/2015 | Greim |
| 9,271,528 B2 | 3/2016 | Liu |
| 9,301,548 B2 | 4/2016 | Liu |
| 9,320,299 B2 | 4/2016 | Hearn et al. |
| 9,423,152 B2 | 8/2016 | Ampolini et al. |
| 9,427,023 B2 | 8/2016 | Liu |
| 9,439,453 B2 | 9/2016 | Conner et al. |
| 9,497,991 B2 | 11/2016 | Besso et al. |
| 9,499,332 B2 | 11/2016 | Fernando et al. |
| 9,504,279 B2 | 11/2016 | Chen |
| 9,516,899 B2 | 12/2016 | Plojoux et al. |
| 9,532,603 B2 | 1/2017 | Plojoux et al. |
| 9,560,883 B2 | 2/2017 | Hawes |
| 9,603,388 B2 | 3/2017 | Fernando et al. |
| 9,655,383 B2 | 5/2017 | Holzherr et al. |
| 9,693,587 B2 | 7/2017 | Plojoux et al. |
| 9,723,871 B2 | 8/2017 | Xiang |
| 9,795,166 B2 | 10/2017 | Liu |
| 9,814,263 B2 | 11/2017 | Cochand et al. |
| 9,854,841 B2 | 1/2018 | Ampolini et al. |
| 9,854,845 B2 | 1/2018 | Plojoux et al. |
| 9,894,934 B2 | 2/2018 | Li et al. |
| 9,903,071 B2 | 2/2018 | Kominami |
| 9,912,955 B2 | 3/2018 | Song et al. |
| 9,918,494 B2 | 3/2018 | Mironov et al. |
| 9,955,724 B2 | 5/2018 | Lord |
| 9,986,760 B2 | 6/2018 | Macko et al. |
| 9,999,247 B2 | 6/2018 | Ruscio et al. |
| 10,015,990 B2 | 7/2018 | Mironov |
| 10,031,183 B2 | 7/2018 | Novak, III et al. |
| 10,070,667 B2 | 9/2018 | Lord et al. |
| 10,104,911 B2 | 10/2018 | Thorens et al. |
| 10,130,780 B2 | 11/2018 | Talon |
| 10,136,673 B2 | 11/2018 | Mironov |
| 10,159,283 B2 | 12/2018 | Mironov |
| 10,194,697 B2 | 2/2019 | Fernando et al. |
| 10,299,513 B2 | 5/2019 | Perez et al. |
| 10,368,584 B2 | 8/2019 | Fernando et al. |
| 10,439,419 B2 | 10/2019 | Bernauer et al. |
| 10,440,987 B2 | 10/2019 | Zeng et al. |
| 10,448,670 B2 | 10/2019 | Talon et al. |
| 10,492,542 B1 | 12/2019 | Worm et al. |
| 10,548,350 B2 | 2/2020 | Greim et al. |
| 10,555,553 B2 | 2/2020 | Binassi et al. |
| 10,555,555 B2 | 2/2020 | Fernando et al. |
| 10,588,351 B2 | 3/2020 | Ricketts |
| 10,617,149 B2 | 4/2020 | Malgat et al. |
| 10,645,971 B2 | 5/2020 | Zitzke |
| 10,668,058 B2 | 6/2020 | Rose et al. |
| 10,716,329 B2 | 7/2020 | Matsumoto et al. |
| 10,757,975 B2 | 9/2020 | Batista et al. |
| 10,813,174 B2 | 10/2020 | Schneider et al. |
| 10,881,143 B2 | 1/2021 | Suzuki et al. |
| 11,039,642 B2 | 6/2021 | Zuber et al. |
| 11,147,316 B2 | 10/2021 | Farine et al. |
| 11,445,576 B2 | 9/2022 | Zinovik et al. |
| 11,627,759 B2 | 4/2023 | Han et al. |
| 2004/0261802 A1 | 12/2004 | Griffin et al. |
| 2005/0045198 A1 | 3/2005 | Larson et al. |
| 2005/0172976 A1 | 8/2005 | Newman et al. |
| 2006/0030214 A1 | 2/2006 | Katou et al. |
| 2008/0001052 A1 | 1/2008 | Kalous et al. |
| 2009/0283103 A1 | 11/2009 | Nielsen et al. |
| 2010/0001538 A1 | 1/2010 | Kim et al. |
| 2010/0024834 A1 | 2/2010 | Oglesby et al. |
| 2010/0242977 A1 | 9/2010 | Tarora et al. |
| 2010/0307518 A1 | 12/2010 | Wang |
| 2011/0126848 A1 | 6/2011 | Zuber et al. |
| 2011/0155151 A1 | 6/2011 | Newman et al. |
| 2011/0209717 A1 | 9/2011 | Han |
| 2011/0226236 A1 | 9/2011 | Buchberger |
| 2011/0265806 A1 | 11/2011 | Alarcon et al. |
| 2011/0290248 A1 | 12/2011 | Schennum |
| 2011/0290269 A1 | 12/2011 | Shimizu |
| 2012/0006343 A1 | 1/2012 | Renaud et al. |
| 2012/0048266 A1 | 3/2012 | Alelov |
| 2012/0227753 A1* | 9/2012 | Newton .................. A24F 40/95 131/347 |
| 2012/0247494 A1 | 10/2012 | Oglesby et al. |
| 2012/0325232 A1 | 12/2012 | Yokogawa et al. |
| 2013/0014772 A1* | 1/2013 | Liu .................. A24F 40/30 131/329 |
| 2013/0037041 A1 | 2/2013 | Worm et al. |

(56) References Cited

U.S. PATENT DOCUMENTS

| | | |
|---|---|---|
| 2013/0074857 A1 | 3/2013 | Buchberger |
| 2013/0213419 A1 | 8/2013 | Tucker et al. |
| 2013/0233329 A1 | 9/2013 | Sebastian et al. |
| 2013/0284192 A1 | 10/2013 | Peleg et al. |
| 2013/0319439 A1 | 12/2013 | Gorelick et al. |
| 2013/0319999 A1 | 12/2013 | Plojoux et al. |
| 2013/0340775 A1 | 12/2013 | Juster et al. |
| 2014/0014125 A1 | 1/2014 | Fernando et al. |
| 2014/0020698 A1 | 1/2014 | Fiebelkorn |
| 2014/0096782 A1 | 4/2014 | Ampolini et al. |
| 2014/0101960 A1 | 4/2014 | Kida et al. |
| 2014/0116455 A1 | 5/2014 | Youn |
| 2014/0246035 A1 | 9/2014 | Minskoff et al. |
| 2014/0299137 A1 | 10/2014 | Kieckbusch et al. |
| 2014/0301721 A1 | 10/2014 | Ruscio et al. |
| 2014/0305448 A1 | 10/2014 | Zuber et al. |
| 2014/0318559 A1 | 10/2014 | Thorens et al. |
| 2014/0345633 A1 | 11/2014 | Talon et al. |
| 2014/0345634 A1 | 11/2014 | Zuber et al. |
| 2014/0363145 A1 | 12/2014 | Plojoux et al. |
| 2015/0007838 A1 | 1/2015 | Fernando et al. |
| 2015/0013696 A1 | 1/2015 | Plojoux et al. |
| 2015/0020832 A1 | 1/2015 | Greim et al. |
| 2015/0027474 A1 | 1/2015 | Zuber et al. |
| 2015/0024355 A1 | 2/2015 | Ghofrani et al. |
| 2015/0059996 A1 | 3/2015 | Zitturi et al. |
| 2015/0100441 A1 | 4/2015 | Alarcon et al. |
| 2015/0136124 A1 | 5/2015 | Aronie et al. |
| 2015/0136154 A1 | 5/2015 | Mitrev et al. |
| 2015/0189910 A1 | 7/2015 | Sebastian et al. |
| 2015/0201676 A1 | 7/2015 | Shin |
| 2015/0208725 A1 | 7/2015 | Tsai |
| 2015/0208730 A1 | 7/2015 | Li et al. |
| 2015/0245654 A1 | 9/2015 | Memari et al. |
| 2015/0245666 A1 | 9/2015 | Memari et al. |
| 2015/0257455 A1 | 9/2015 | Henry, Jr. et al. |
| 2015/0272211 A1 | 10/2015 | Chung |
| 2015/0296878 A1 | 10/2015 | Mucalo et al. |
| 2015/0359259 A1 | 12/2015 | Conner et al. |
| 2016/0150824 A1 | 6/2016 | Memari et al. |
| 2016/0205998 A1 | 7/2016 | Matsumoto et al. |
| 2016/0213066 A1* | 7/2016 | Zitzke ............... A61M 11/042 |
| 2016/0235121 A1 | 8/2016 | Rogan et al. |
| 2016/0270437 A1 | 9/2016 | Nappi |
| 2016/0286861 A1 | 10/2016 | Liu |
| 2016/0302488 A1 | 10/2016 | Fernando et al. |
| 2016/0031032 A1 | 11/2016 | Malgat et al. |
| 2016/0331032 A1 | 11/2016 | Malgat et al. |
| 2016/0345629 A1 | 12/2016 | Mironov |
| 2016/0366933 A1 | 12/2016 | Liu |
| 2016/0366937 A1 | 12/2016 | Liu |
| 2016/0366946 A1 | 12/2016 | Murison et al. |
| 2016/0374402 A1 | 12/2016 | Fernando et al. |
| 2017/0006916 A1 | 1/2017 | Liu |
| 2017/0006919 A1 | 1/2017 | Liu |
| 2017/0027229 A1 | 2/2017 | Cameron |
| 2017/0027234 A1 | 2/2017 | Farine et al. |
| 2017/0042243 A1 | 2/2017 | Plojoux et al. |
| 2017/0042251 A1 | 2/2017 | Yamada et al. |
| 2017/0055580 A1 | 3/2017 | Blandino et al. |
| 2017/0065002 A1 | 3/2017 | Fernando et al. |
| 2017/0071251 A1 | 3/2017 | Goch |
| 2017/0071259 A1 | 3/2017 | Yamada et al. |
| 2017/0095006 A1 | 4/2017 | Egoyants et al. |
| 2017/0150757 A1 | 6/2017 | Worm et al. |
| 2017/0164659 A1 | 6/2017 | Schneider et al. |
| 2017/0172214 A1 | 6/2017 | Li et al. |
| 2017/0172215 A1 | 6/2017 | Li et al. |
| 2017/0188634 A1 | 7/2017 | Plojoux et al. |
| 2017/0238596 A1 | 8/2017 | Matsumoto et al. |
| 2017/0295844 A1 | 10/2017 | Thevenaz et al. |
| 2018/0153216 A1 | 6/2018 | Wong et al. |
| 2018/0177234 A1 | 6/2018 | Lee |
| 2018/0206556 A1 | 7/2018 | Thorens et al. |
| 2018/0235283 A1 | 8/2018 | Zuber et al. |
| 2018/0280653 A1 | 10/2018 | Buchberger |
| 2019/0014826 A1 | 1/2019 | Thorens et al. |
| 2019/0075849 A1 | 3/2019 | Hawes |
| 2019/0297937 A1* | 10/2019 | Guyard ............... A24D 3/14 |
| 2019/0320719 A1 | 10/2019 | Liu et al. |
| 2019/0364975 A1 | 12/2019 | Fernando et al. |
| 2020/0006950 A1 | 1/2020 | Holzherr |
| 2020/0008475 A1 | 1/2020 | Lai et al. |
| 2020/0008480 A1 | 1/2020 | Batista |
| 2020/0120983 A1 | 4/2020 | Chen |
| 2020/0154765 A1 | 5/2020 | Lee et al. |
| 2020/0232766 A1 | 7/2020 | Flick |
| 2020/0305508 A1 | 10/2020 | Talon |
| 2020/0352224 A1 | 11/2020 | Plojoux et al. |
| 2020/0352231 A1 | 11/2020 | Han et al. |
| 2020/0359681 A1 | 11/2020 | Han et al. |
| 2020/0359682 A1 | 11/2020 | Han et al. |
| 2020/0413495 A1 | 12/2020 | Schneider et al. |
| 2021/0000182 A1 | 1/2021 | Ruscio et al. |
| 2021/0077752 A1 | 3/2021 | Buchberger |
| 2021/0120875 A1 | 4/2021 | Mironov |
| 2022/0087309 A1 | 3/2022 | Han et al. |
| 2022/0117293 A1 | 4/2022 | Zuber et al. |

FOREIGN PATENT DOCUMENTS

| | | |
|---|---|---|
| CH | 310239 A | 12/1955 |
| CN | 2146758 Y | 11/1993 |
| CN | 1102964 A | 5/1995 |
| CN | 1122213 A | 5/1996 |
| CN | 1190335 A | 8/1998 |
| CN | 1209731 A | 3/1999 |
| CN | 1205388 C | 6/2005 |
| CN | 1212785 C | 8/2005 |
| CN | 2857109 Y | 1/2007 |
| CN | 1973706 A | 6/2007 |
| CN | 101043827 A | 9/2007 |
| CN | 101444335 A | 6/2009 |
| CN | 201467999 U | 5/2010 |
| CN | 201491717 U | 6/2010 |
| CN | 101896082 A | 11/2010 |
| CN | 101940369 A | 1/2011 |
| CN | 102006790 A | 4/2011 |
| CN | 102109393 A | 6/2011 |
| CN | 102216526 A | 12/2011 |
| CN | 102326869 A | 1/2012 |
| CN | 102438470 A | 5/2012 |
| CN | 102481021 A | 5/2012 |
| CN | 202407082 U | 9/2012 |
| CN | 102762118 A | 10/2012 |
| CN | 102821632 A | 12/2012 |
| CN | 202774134 U | 3/2013 |
| CN | 103096741 A | 5/2013 |
| CN | 103281920 A | 9/2013 |
| CN | 103338665 A | 10/2013 |
| CN | 103501644 A | 1/2014 |
| CN | 103622162 A | 3/2014 |
| CN | 203457802 U | 3/2014 |
| CN | 103717802 A | 4/2014 |
| CN | 103717803 A | 4/2014 |
| CN | 203563687 U | 4/2014 |
| CN | 203575658 U | 5/2014 |
| CN | 103859606 A | 6/2014 |
| CN | 203633505 U | 6/2014 |
| CN | 203646503 U | 6/2014 |
| CN | 103929988 A | 7/2014 |
| CN | 103929989 A | 7/2014 |
| CN | 203689071 U | 7/2014 |
| CN | 203692545 U | 7/2014 |
| CN | 103974638 A | 8/2014 |
| CN | 103974640 A | 8/2014 |
| CN | 103987286 A | 8/2014 |
| CN | 103997921 A | 8/2014 |
| CN | 103997922 A | 8/2014 |
| CN | 203789137 U | 8/2014 |
| CN | 104023568 A | 9/2014 |
| CN | 104023574 A | 9/2014 |
| CN | 203814592 U | 9/2014 |
| CN | 104135882 A | 11/2014 |

(56) References Cited

FOREIGN PATENT DOCUMENTS

| | | |
|---|---|---|
| CN | 203943078 U | 11/2014 |
| CN | 104203015 A | 12/2014 |
| CN | 204070570 U | 1/2015 |
| CN | 204146338 U | 2/2015 |
| CN | 102811634 B | 3/2015 |
| CN | 104382237 A | 3/2015 |
| CN | 104470387 A | 3/2015 |
| CN | 104489933 A | 4/2015 |
| CN | 104544559 A | 4/2015 |
| CN | 204317494 U | 5/2015 |
| CN | 104754964 A | 7/2015 |
| CN | 104770878 A | 7/2015 |
| CN | 104799438 A | 7/2015 |
| CN | 104812260 A | 7/2015 |
| CN | 204444239 U | 7/2015 |
| CN | 104839886 A | 8/2015 |
| CN | 104869854 A | 8/2015 |
| CN | 104886775 A | 9/2015 |
| CN | 104902767 A | 9/2015 |
| CN | 204763414 U | 11/2015 |
| CN | 105163610 A | 12/2015 |
| CN | 105208882 A | 12/2015 |
| CN | 105208884 A | 12/2015 |
| CN | 105341993 A | 2/2016 |
| CN | 105357994 A | 2/2016 |
| CN | 105361250 A | 3/2016 |
| CN | 105453598 A | 3/2016 |
| CN | 205072064 U | 3/2016 |
| CN | 205180371 U | 4/2016 |
| CN | 205197003 U | 5/2016 |
| CN | 105722416 A | 6/2016 |
| CN | 205337598 U | 6/2016 |
| CN | 105747281 A | 7/2016 |
| CN | 105789506 A | 7/2016 |
| CN | 105831812 A | 8/2016 |
| CN | 105848503 A | 8/2016 |
| CN | 105852223 A | 8/2016 |
| CN | 105876869 A | 8/2016 |
| CN | 205456048 U | 8/2016 |
| CN | 205512358 U | 8/2016 |
| CN | 105939625 A | 9/2016 |
| CN | 205597118 U | 9/2016 |
| CN | 106037014 A | 10/2016 |
| CN | 205648910 U | 10/2016 |
| CN | 205658366 U | 10/2016 |
| CN | 104135881 B | 11/2016 |
| CN | 106102492 A | 11/2016 |
| CN | 106132217 A | 11/2016 |
| CN | 106136332 A | 11/2016 |
| CN | 106163307 A | 11/2016 |
| CN | 106174699 A | 12/2016 |
| CN | 106231934 A | 12/2016 |
| CN | 106255430 A | 12/2016 |
| CN | 205831062 U | 12/2016 |
| CN | 205884659 U | 1/2017 |
| CN | 106376975 A | 2/2017 |
| CN | 106413439 A | 2/2017 |
| CN | 106413444 A | 2/2017 |
| CN | 106455708 A | 2/2017 |
| CN | 106455714 A | 2/2017 |
| CN | 106455716 A | 2/2017 |
| CN | 106473233 A | 3/2017 |
| CN | 106535680 A | 3/2017 |
| CN | 206025202 U | 3/2017 |
| CN | 206097720 U | 4/2017 |
| CN | 206197012 U | 5/2017 |
| CN | 106858726 A | 6/2017 |
| CN | 106901404 A | 6/2017 |
| CN | 206312988 U | 7/2017 |
| CN | 107080292 A | 8/2017 |
| CN | 206443202 U | 8/2017 |
| CN | 206472849 U | 9/2017 |
| CN | 2017220157 U | 4/2018 |
| CN | 105342011 B | 6/2018 |
| CN | 207836767 U | 9/2018 |
| CN | 208192123 U | 12/2018 |
| CN | 208192126 U | 12/2018 |
| CN | 110494053 B | 5/2022 |
| DE | 3302518 A1 | 7/1984 |
| DE | 20 2014 004 361 U1 | 10/2015 |
| EA | 012169 B1 | 8/2009 |
| EA | 026076 B1 | 2/2017 |
| EP | 1 119 267 B1 | 7/2004 |
| EP | 1 964 482 A1 | 9/2008 |
| EP | 2 110 033 A1 | 10/2009 |
| EP | 2113178 A1 | 11/2009 |
| EP | 2 201 850 A1 | 6/2010 |
| EP | 2253233 A1 | 11/2010 |
| EP | 2316286 A1 | 5/2011 |
| EP | 2 022 349 B1 | 7/2014 |
| EP | 2 875 740 A2 | 5/2015 |
| EP | 2 531 053 B1 | 9/2015 |
| EP | 2921065 A1 | 9/2015 |
| EP | 2 740 370 B1 | 4/2016 |
| EP | 3 098 738 A1 | 11/2016 |
| EP | 2 432 339 B1 | 3/2017 |
| EP | 3 179 828 A1 | 6/2017 |
| EP | 3 632 237 A1 | 4/2020 |
| EP | 3 632 239 A1 | 4/2020 |
| EP | 3 275 319 B1 | 8/2020 |
| EP | 377055 A1 | 10/2020 |
| GB | 2542018 A | 3/2017 |
| GB | 2550540 A | 11/2017 |
| JP | 2-190178 A | 7/1990 |
| JP | 3-232481 A | 10/1991 |
| JP | 6-209756 A | 8/1994 |
| JP | 7-184627 A | 7/1995 |
| JP | H11-40122 A | 2/1999 |
| JP | 11-164679 A | 6/1999 |
| JP | 3645921 B2 | 5/2005 |
| JP | 2006-92831 A | 4/2006 |
| JP | 2006-320286 A | 11/2006 |
| JP | 4278306 B2 | 6/2009 |
| JP | 4728306 B2 | 6/2009 |
| JP | 2010-178730 A | 8/2010 |
| JP | 2010-526553 A | 8/2010 |
| JP | 2011-87569 A | 5/2011 |
| JP | 2011-518567 A | 6/2011 |
| JP | 4739433 B2 | 8/2011 |
| JP | 2012-506263 A | 3/2012 |
| JP | 2012-527222 A | 11/2012 |
| JP | 2014-500017 A | 1/2014 |
| JP | 2014-79229 A | 5/2014 |
| JP | 2014-511175 A | 5/2014 |
| JP | 2014-521419 A | 8/2014 |
| JP | 2014-525237 A | 9/2014 |
| JP | 2014-533513 A | 12/2014 |
| JP | 2014-534813 A | 12/2014 |
| JP | 2015-503335 A | 2/2015 |
| JP | 2015-503916 A | 2/2015 |
| JP | 2015-504669 A | 2/2015 |
| JP | 2015-506170 A | 3/2015 |
| JP | 2015-507477 A | 3/2015 |
| JP | 2015-508996 A | 3/2015 |
| JP | 2015-524261 A | 8/2015 |
| JP | 2015-156806 A | 9/2015 |
| JP | 2015-180214 A | 10/2015 |
| JP | 2015-529458 A | 10/2015 |
| JP | 2015-204833 A | 11/2015 |
| JP | 2016-528910 A | 9/2016 |
| JP | 3207506 U | 11/2016 |
| JP | 2016-538848 A | 12/2016 |
| JP | 2017-501682 A | 1/2017 |
| JP | 2017-46700 A | 3/2017 |
| JP | 2017-51189 A | 3/2017 |
| JP | 2017-70297 A | 4/2017 |
| JP | 2017-514463 A | 6/2017 |
| JP | 2021-153586 A | 10/2021 |
| KR | 1999-007914 A | 1/1999 |
| KR | 10-0304044 B1 | 11/2001 |
| KR | 10-0636287 B1 | 10/2006 |
| KR | 10-0806461 B1 | 2/2008 |
| KR | 20-2009-0008911 U | 9/2009 |
| KR | 10-0965099 B1 | 6/2010 |

(56) References Cited

FOREIGN PATENT DOCUMENTS

| | | |
|---|---|---|
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0080285 A | 7/2012 |
| KR | 10-2012-0101637 A | 9/2012 |
| KR | 10-1184499 B1 | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 20-0466757 Y1 | 5/2013 |
| KR | 10-2013-0081238 A | 7/2013 |
| KR | 20-0469513 Y1 | 10/2013 |
| KR | 10-2013-0139296 A | 12/2013 |
| KR | 10-2014-0015774 A | 2/2014 |
| KR | 10-1383577 B1 | 4/2014 |
| KR | 10-2014-0068203 A | 6/2014 |
| KR | 10-2014-0092312 A | 7/2014 |
| KR | 10-2014-0114554 A | 9/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 20-2014-0006242 U | 12/2014 |
| KR | 10-2015-0030409 A | 3/2015 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-1523088 B2 | 5/2015 |
| KR | 10-2015-0099704 A | 9/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0040643 A | 4/2016 |
| KR | 10-1609715 B1 | 4/2016 |
| KR | 10-2016-0052607 A | 5/2016 |
| KR | 10-2016-0060006 A | 5/2016 |
| KR | 10-1619032 B1 | 5/2016 |
| KR | 20-2016-0001476 U | 5/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-2016-0110670 A | 9/2016 |
| KR | 10-1656061 B1 | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-2017-0071486 A | 6/2017 |
| KR | 10-2017-0074898 A | 6/2017 |
| KR | 10-1740160 B1 | 6/2017 |
| KR | 10-2017-0119664 A | 10/2017 |
| KR | 10-2018-0070457 A | 6/2018 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2 603 559 C2 | 11/2016 |
| RU | 2 604 012 C2 | 12/2016 |
| UA | 112169 C2 | 8/2016 |
| WO | 94/06314 A1 | 3/1994 |
| WO | 95/33246 A1 | 12/1995 |
| WO | 98/23171 A1 | 6/1998 |
| WO | 2010/133342 A1 | 11/2010 |
| WO | 2011/028372 A1 | 3/2011 |
| WO | 2011/050964 A1 | 5/2011 |
| WO | 2011/095781 A1 | 8/2011 |
| WO | 2012/072264 A1 | 6/2012 |
| WO | 2012/123702 A1 | 9/2012 |
| WO | 2012/126721 A1 | 9/2012 |
| WO | 2013/021863 A1 | 2/2013 |
| WO | 2013/034458 A1 | 3/2013 |
| WO | 2013/060743 A2 | 5/2013 |
| WO | 2013/076098 A2 | 5/2013 |
| WO | 2013/093695 A1 | 6/2013 |
| WO | 2013/098395 A1 | 7/2013 |
| WO | 2013/098396 A2 | 7/2013 |
| WO | 2013/098397 A2 | 7/2013 |
| WO | 2013/098398 A3 | 7/2013 |
| WO | 2013/098409 A1 | 7/2013 |
| WO | 2013/102612 A2 | 7/2013 |
| WO | 2013102609 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/171217 A1 | 11/2013 |
| WO | 2013/190036 A1 | 12/2013 |
| WO | 2014/029880 A2 | 2/2014 |
| WO | 2014/102092 A1 | 7/2014 |
| WO | 2015/046386 A1 | 4/2015 |
| WO | 2015/088744 A1 | 6/2015 |
| WO | 2015/092071 A1 | 6/2015 |
| WO | 2015/117704 A1 | 8/2015 |
| WO | 2015/128665 A1 | 9/2015 |
| WO | 2015/155289 A1 | 10/2015 |
| WO | 2015/165813 A1 | 11/2015 |
| WO | 2015/174657 A1 | 11/2015 |
| WO | 2015/177044 A1 | 11/2015 |
| WO | 2015/197627 A1 | 12/2015 |
| WO | 2016/012811 A1 | 1/2016 |
| WO | 2016/055653 A1 | 4/2016 |
| WO | 2016/059073 A1 | 4/2016 |
| WO | 2016/075028 A1 | 5/2016 |
| WO | 2016/076147 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016-156121 A1 | 10/2016 |
| WO | 2016/156219 A1 | 10/2016 |
| WO | 2016/159013 A1 | 10/2016 |
| WO | 2016/166064 A1 | 10/2016 |
| WO | 2016/178377 A1 | 11/2016 |
| WO | 2016/187803 A1 | 12/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/075759 A1 | 5/2017 |
| WO | 2017-075975 A1 | 5/2017 |
| WO | 2017/139963 A1 | 8/2017 |
| WO | 2018/050449 A1 | 3/2018 |
| WO | 2018/189195 A1 | 10/2018 |
| WO | 2019-014991 A1 | 1/2019 |
| WO | 2019/020826 A1 | 1/2019 |
| WO | 2019/030172 A1 | 2/2019 |
| WO | 2019/095268 A1 | 5/2019 |
| WO | 2019-121808 A1 | 6/2019 |

(56) References Cited

FOREIGN PATENT DOCUMENTS

OTHER PUBLICATIONS

Office Action issued Nov. 14, 2019 in Korean Application No. 10-2017-0084385.
Office Action issued Nov. 14, 2019 in Korean Application No. 10-2017-0147605.
Office Action issued Dec. 11, 2019 in Korean Application No. 10-2018-0010836.
Office Action issued Dec. 11, 2019 in Korean Application No. 10-2018-0010841.
Office Action issued Dec. 19, 2019 in Korean Application No. 10-2018-0090910.
Office Action issued Jan. 3, 2020 in Korean Application No. 10-2018-0012456.
Office Action issued Jan. 3, 2020 in Korean Application No. 10-2017-0084389.
Office Action issued Jan. 3, 2020 in Korean Application No. 10-2017-0084386.
Office Action issued Jan. 3, 2020 in Korean Application No. 10-2018-0018693.
Office Action issued Jan. 8, 2020 in Korean Application No. 10-2017-0128293.
Office Action issued Jan. 8, 2020 in Korean Application No. 10-2017-0119664.
Office Action issued Jan. 16, 2020 in Korean Application No. 10-2017-0084388.
Office Action issued Jan. 16, 2020 in Korean Application No. 10-2017-0084387.
Office Action issued Feb. 11, 2020 in Korean Application No. 10-2018-0010834.
Office Action issued Feb. 11, 2020 in Korean Application No. 10-2018-0010835.
Office Action issued Feb. 13, 2020 in Korean Application No. 10-2018-0010837.
Office Action issued Feb. 18, 2020 in Russian Application No. 2019121813.
Office Action dated Aug. 7, 2019 for Korean Patent Application No. 10-2018-0067035, and its English translation provided by Applicants foreign counsel.
Office Action dated Jun. 27, 2019 for Korean Patent Application No. 10-2018-0063759, and its English translation provided by Applicants foreign counsel.
Office Action dated Jul. 2, 2019 for Korean Patent Application No. 10-2019-0018815, and its English translation provided by Applicants foreign counsel.
Office Action dated Jul. 3, 2019 for Korean Patent Application No. 10-2019-0017391, and its English translation provided by Applicants foreign counsel.
International Preliminary Report on Patentability (Chapter I) issued on Jun. 18, 2019 for PCT/KR2017/012486 and its English translation from WIPO.
Written Opinion of the International Searching Authority for PCT/KR2017/012486 mailed May 29, 2018 and its English translation by Google Translate (now published as WO 2018/110834).
Partial supplementary European search report issued Aug. 3, 2020 in Application No. 17880867.1.
Extended European search report issued Nov. 4, 2020 by the European Patent Office in Application No. 17880867.1.
Office Action issued Oct. 29, 2020 by the Korean Patent Office in Application No. 10-2018-0010837.
Office Action issued Nov. 4, 2020 by the Japanese Patent Office in Application No. 2019-554453.
Office Action issued Nov. 4, 2020 by the Japanese Patent Office in Application No. 2020-128346.
Decision on Grant issued Nov. 26, 2020 by the Russian Federal Service For Intellectual Property Patent Application No. 2020124607.
Office Action issued Nov. 26, 2020 by Russian Federal Service For Intellectual Property Office Patent Application No. 2020124609.
Decision on Grant issued Oct. 26, 2020 by Russian Federal Service For Intellectual Property in Application No. 2020124610.
Office Action issued Jun. 29, 2020 by the Korean Patent Office in Application No. 10-2018-0010836.
Extended European Search Report issued Dec. 11, 2020 in European Application No. 20188967.2.
Extended European Search Report issued Jan. 15, 2021 in European Application No. 20188949.0.
Extended European Search Report issued Dec. 16, 2020 in European Application No. 20188985.4.
Office Action issued Dec. 30, 2020 in Russian Application No. 2020124651.
Office Action issued Dec. 28, 2020 in Russian Application No. 2020124652.
Office Action issued Dec. 11, 2020 in Russian Application No. 2020124653.
Office Action issued Jan. 22, 2021 in Russian Application No. 2020124657.
Office Action issued Jan. 22, 2021 in Russian Application No. 2020124658.
Extended European Search Report issued Dec. 18, 2020 in European Application No. 18775504.6.
Office Action issued Jan. 19, 2021 in Japanese Application No. 2019-553569.
Extended European Search Report issued Jan. 14, 2021 in European Application No. 18784738.9.
Extended European Search Report issued Dec. 10, 2020 in European Application No. 20188932.6.
Office Action issued Jan. 12, 2021 in Japanese Application No. 2019-555201.
Office Action issued Jan. 12, 2021 in Japanese Application No. 2019-555169.
Office Action issued Jan. 5, 2021 in Japanese Application No. 2019-558557.
Extended European Search Report issued Nov. 19, 2020 in European Application No. 20188792.4.
Office Action issued Dec. 1, 2020 in Japanese Application No. 2020-501188.
Extended European Search Report issued Dec. 18, 2020 in European Application No. 20188926.8.
Office Action issued Jan. 19, 2021 in Japanese Application No. 2020-501514.
Office Action issued Sep. 24, 2020 in Korean Application No. 10-2018-0012456.
Office Action issued May 28, 2020 in Korean Application No. 10-2017-0147605.
Extended European Search Report issued Jan. 14, 2021 in European Application No. 18783776.0.
Extended European Search Report issued Jan. 25, 2021 in European Application No. 18785166.2.
Extended European Search Report issued Jan. 29, 2021 in European Application No. 18784464.2.
Extended European Search Report issued Mar. 15, 2021 in European Application No. 18785061.5.
Extended European Search Report issued Mar. 19, 2021 in European Application No. 18784164.8.
Extended European Search Report issued Mar. 24, 2021 in European Application No. 18784268.7.
Extended European Search Report issued Mar. 25, 2021 in European Application No. 18784370.1.
Extended European Search Report issued Mar. 25, 2021 in European Application No. 18784841.1.
Office Action issued Feb. 24, 2021 in Japanese Application No. 2019-555168.
Office Action issued Feb. 24, 2021 in Japanese Application No. 2019-555203.
Office Action issued Feb. 24, 2021 in Japanese Application No. 2019-555204.
Office Action issued Feb. 4, 2021 in Russian Application No. 2020124609.
Office Action issued Feb. 9, 2021 in Japanese Application No. 2019-555184.

(56) References Cited

OTHER PUBLICATIONS

Office Action issued Jan. 19, 2021 in Indonesian Application No. P00201906007.
Office Action issued Jan. 26, 2021 in Japanese Application No. 2020-501521.
Office Action issued Mar. 2, 2021 in Japanese Application No. 2019-555170.
Office Action issued Mar. 2, 2021 in Japanese Application No. 2019-555182.
Office Action issued Mar. 30, 2021 in Japanese Application No. 2020-501377.
International Search Report issued Jul. 24, 2018 in International Application No. PCT/KR2018/003691.
Office Action issued Jul. 2, 2019 in Korean Application No. 10-2019-0018815.
Office Action issued Jul. 3, 2019 in Korean Application No. 10-2019-0017391.
International Search Report issued Oct. 29, 2018 in International Application No. PCT/KR2018/004181.
International Search Report issued Sep. 6, 2018 in International Application No. PCT/KR2018/004179.
International Search Report issued Nov. 6, 2018 in International Application No. PCT/KR2018/004178.
International Search Report issued Sep. 6, 2018 in International Application No. PCT/KR2018/004176.
International Search Report issued Sep. 7, 2018 in International Application No. PCT/KR2018/004172.
International Search Report issued Sep. 7, 2018 in International Application No. PCT/KR2018/004171.
International Search Report issued Nov. 6, 2018 in International Application No. PCT/KR2018/004130.
International Search Report issued Nov. 6, 2018 in International Application No. PCT/KR2018/004129.
International Search Report issued Nov. 14, 2018 in International Application No. PCT/KR2018/004118.
International Search Report issued May 29, 2018 in International Application No. PCT/KR2017/012486.
Office Action issued Sep. 29, 2021 in Chinese Application No. 201880024311.8.
Office Action issued Sep. 24, 2021 in Chinese Application No. 201880024010.5.
Office Action issued Sep. 29, 2021 in Chinese Application No. 201880024276.X.
Office Action issued Oct. 28, 2021 in Chinese Application No. 201880046418.2.
Extended European Search Report issued Oct. 27, 2021 in European Application No. 18844735.3.
Office Action issued Sep. 17, 2021 in Chinese Application No. 201880030699.2.
Communication dated Apr. 4, 2019, issued by the Korean Intellectual Property Office in application No. 10-2019-0019194.
Communication dated Apr. 4, 2019, issued by the Korean Intellectual Property Office in application No. 10-2019-0019195.
Communication dated Apr. 5, 2019, issued by the Korean Intellectual Property Office in application No. 10-2019-0027638.
Communication dated Apr. 25, 2019, issued by the Korean Intellectual Property Office in application No. 10-2019-0033784.
Communication dated Apr. 9, 2021, issued by the Korean Intellectual Property Office in application No. 10-2020-0116256.
Communication dated Jul. 22, 2021, issued by the Korean Intellectual Property Office in application No. 10-2021-0051359.
Communication dated May 5, 2021, issued by the Canadian Patent Office in application No. 3,047,236.
Extended European Search Report dated Jan. 15, 2021, issued by the European Patent Office in application No. 20188949.0.
Communication dated Jun. 10, 2021, issued by the Federal Service for Intellectual Property in Russian application No. 2020124657/03.
Communication dated Jun. 10, 2021, issued by the Federal Service for Intellectual Property in Russian application No. 2020124658/03.
Communication dated Jun. 29, 2021, issued by the State Intellectual Property Office of the P.R.C. in application No. 201880022072.2.
Extended European Search Report dated Apr. 1, 2021, issued by the European Patent Office in application No. 18805933.1.
Extended European Search Report dated Jun. 16, 2021, issued by the European Patent Office in application No. 18853434.1.
Extended European Search Report dated Jul. 1, 2021, issued by the European Patent Office in application No. 18854661.8.
Extended European Search Report dated Jun. 14, 2021, issued by the European Patent Office in application 18842951.8.
International Search Report dated Nov. 6, 2018, issued by the International Searching Authority in application No. PCT/KR2018/004129.
International Search Report dated Aug. 29, 2018, issued by the International Searching Authority in application No. PCT/KR2018/005945.
International Search Report dated Nov. 30, 2018, issued by the International Searching Authority in application No. PCT/KR2018/006702.
International Search Report dated Dec. 6, 2018, issued by the International Searching Authority in application No. PCT/KR2018/006747.
International Search Report dated Nov. 26, 2018, issued by the International Searching Authority in application No. PCT/KR2018/009094.
International Search Report dated Feb. 28, 2019, issued by the International Searching Authority in application No. PCT/KR2018/009100.
Communication dated Jul. 27, 2021, issued by the State Intellectual Property Office of the P.R.C. in application No. 201780084891.5.
Communication dated Aug. 16, 2021, issued by the State Intellectual Property Office of the P.R.C. in application No. 201880024006.9.
Communication dated Aug. 26, 2021, issued by the State Intellectual Property Office of the P.R.C. in application No. 201880024107.6.
Communication dated Aug. 4, 2021, issued by the State Intellectual Property Office of the P.R.C. in application No. 201880024289.7.
Communication dated Jul. 26, 2021, issued by the State Intellectual Property Office of the P.R.C. in application No. 201880024059.0.
Communication dated Jul. 16, 2021, issued by the State Intellectual Property Office of the P.R.C. in application No. 201880024367.3.
Communication dated Jul. 19, 2021, issued by the State Intellectual Property Office of the P.R.C. in application No. 201880024070.7.
Office Action dated Jun. 28, 2022 issued by the Japanese Patent Office in Japanese Application No. 2021-075028.
Office Action dated Jun. 9, 2022 issued by the Philippine Patent Office in Philippine Application No. 1/2019/501361.
Notice of Reasons for Refusal dated Sep. 20, 2022 from the Japanese Patent Office in Japanese Application No. 2021-174035.
Communication dated Aug. 12, 2022 from the Chinese Patent Office in Chinese Application No. 201880024059.0.
Office Action issued Mar. 14, 2022 in Chinese Application No. 201880024059.0.
Office Action issued Feb. 28, 2022 in Chinese Application No. 201880050526.7.
Communication dated Dec. 1, 2021 from the Chinese Patent Office in Chinese Application No. 201880046367.3.
Communication dated Nov. 25, 2021 from the Chinese Patent Office in Chinese Application No. 201880047174.X.
Notice of Reasons of Refusal dated Jan. 10, 2023 from the Japanese Patent Office in Application No. 2021-177649.
Office Action dated Jan. 10, 2023 from the Chinese Patent Office in Application No. 202010760990.4.
Office Action dated Jan. 3, 2023 from the Chinese Patent Office in Application No. 202010760979.8.
Office Action dated Jan. 28, 2023 from the Chinese Patent Office in Application No. 202010763214.X.
Office Action dated Nov. 22, 2022 issued by the Chinese Patent Office in Chinese Application No. 202010762996.5.
Office Action dated Oct. 24, 2022 issued by the Ukrainian Patent Office in Ukrainian Application No. 2020 04868.

(56) References Cited

OTHER PUBLICATIONS

English Abstract of Ukrainian Application No. 104628 C2 published on Feb. 25, 2014.
Office Action dated Oct. 27, 2022 issued by the Ukrainian Patent Office in Ukrainian Application No. 2020 04869.
Office Action dated Dec. 30, 2022 issued by the Chinese Patent Office in Chinese Application No. 202010756239.7.
Office Action dated Dec. 13, 2022 issued by the Japanese Patent Office in Japanese Application No. 2021-165298.
Office Action dated Nov. 2, 2022 issued by the Chinese Patent Office in Chinese Application No. 201880050526.7.
Office Action issued Jun. 1, 2023 in Korean Application No. 10-2022-0148790.
Office Action issued Jul. 12, 2023 in Ukrainian Application No. a 2021 04884.
Office Action issued May 9, 2023 in Japanese Application No. 2022-086448.
Communication issued Jul. 10, 2023 in European Application No. 18 785 166.2.
Office Action issued Jul. 31, 2023 in Chinese Application No. 201880050526.7.
Chinese Office Action dated Nov. 3, 2022 in Application No. 201880024276.X.
Chinese Office Action dated Dec. 1, 2023 in Application No. 201880050526.7.
European Office Action dated Dec. 6, 2023 in Application No. 20 188 985.4.
Ukrainian Office Action dated Dec. 21, 2023 in Application No. 202105048.
Chinese Office Action dated Dec. 27, 2023 in Application No. 202010763214.X.
European Office Action dated Nov. 3, 2023 in Application No. 18775504.6.
Chinese Office Action dated Jan. 30, 2024 in Application No. 201721768336.8.
Chinese Office Action dated Jan. 30, 2024 in Application No. 201721768739.2.
Office Action issued Apr. 12, 2024 in Chinese Application No. 201721768740.5.
Office Action issued Feb. 2, 2024 in Chinese Application No. 202010760990.4.
Office Action issued Apr. 23, 2024 in Japanese Application No. 2023-021861.
Office Action issued Mar. 18, 2024 in Ukrainian Application No. a 2021 05048.
Office Action issued Apr. 23, 2024 in Japanese Application No. 2023-006805.
Office Action issued Jul. 23, 2024 in Chinese Application No. 202211609705.4.
Communication issued May 21, 2024 in European Application No. 17 880 867.1.
Office Action issued Jun. 20, 2024 in Filipino Application No. Jan. 2020/551224.
Japanese Office Action dated Oct. 22, 2024 in Application No. 2023-021861.
Communication of a notice of opposition issued in the European Patent Office on Jan. 9, 2025 in corresponding EP Patent Application No. 18805933.1.
First Office Action issued in the State Intellectual Property Office of People's Republic of China on Jan. 23, 2025 in corresponding CN Patent Application No. 202210724458.6.

* cited by examiner

AEROSOL GENERATING APPARATUS AND CRADLE CAPABLE OF RECEIVING SAME

CROSS REFERENCE TO RELATED APPLICATIONS

This application is a National Stage of International Application No. PCT/KR2018/003691 filed Mar. 29, 2018, claiming priority based on Korean Patent Application Nos. 10-2017-0040787 filed Mar. 30, 2017; 10-2017-0046938 filed Apr. 11, 2017; 10-2017-0077586 filed Jun. 19, 2017 and 10-2017-0147605 filed Nov. 7, 2017.

TECHNICAL FIELD

The present disclosure relates to an aerosol generating apparatus and a cradle capable of receiving the same.

BACKGROUND ART

There is a growing demand for a method of generating aerosol by heating an aerosol generating material in a cigarette. Therefore, research into heating-type cigarettes or heating-type aerosol generating apparatuses is actively being carried out.

DESCRIPTION OF EMBODIMENTS

Technical Problem

Provided are an aerosol generating apparatus and a cradle capable of receiving the same.

Solution to Problem

Detailed Description of the Invention

According to an aspect of the present disclosure, an aerosol generating apparatus includes: a cigarette insertion portion into which a cigarette is insertable; and a vaporizer configured to heat a liquid composition to generate aerosol and discharge the generated aerosol toward the inserted cigarette such that the generated aerosol passes through the cigarette inserted into the cigarette insertion portion.

The cigarette insertion portion may include a heater module configured to heat the inserted cigarette to generate the aerosol.

The heater module may be configured to heat the inside of the inserted cigarette to generate the aerosol.

The heater module may be configured to heat the outside of the inserted cigarette to generate the aerosol.

The heater module may be configured to heat the inserted cigarette according to a pulse width modulation (PWM) or a duty cycle of a current supplied from a battery.

The PWM or the duty cycle of the current may be previously set.

The aerosol generating apparatus may further include a sensor configured to detect a puff of a user; and a controller configured to determine, through the sensor, whether the puff of the user has occurred.

The controller may be further configured to determine whether the number of puffs of the user is greater than or equal to a preset puff limit number, and according to a result of the determining, determine whether to terminate operation of the aerosol generating apparatus.

The controller may be further configured to determine whether a number of puffs of the user is equal to or greater than a preset puff limit number, and according to a result of the determining, determine whether to terminate an operation of the aerosol generating apparatus.

The vaporizer may further include a liquid storage unit storing the liquid composition; a liquid transfer means for the liquid composition; a heating element configured to heat the liquid composition transferred by the liquid transfer means to generate aerosol; and an airflow passage arranged to discharge the generated aerosol toward the inserted cigarette.

The aerosol generating apparatus may further include a controller configured to control a current to be supplied to the heating element for a preset period of time from when a puff of a user is detected.

The cigarette may include: a first filter segment; a tobacco rod including an aerosol generating material and a tobacco raw material; a second filter segment including at least one aroma capsule; a third filter segment including a hollow; and a wrapper.

The tobacco rod may be taste-controlled, and at least one of the first filter segment, the tobacco rod, the second filter segment, the third filter segment, and the wrapper may be flavored.

The aerosol generating apparatus may further include an air inflow passage which is a passage for air introduced from outside.

According to another aspect of the present disclosure, a cradle may include: an inner space capable of receiving an aerosol generating apparatus; a battery configured to supply power to charge the aerosol generating apparatus; and a control unit, wherein the aerosol generating apparatus includes a cigarette insertion portion into which a cigarette is insertable; and a vaporizer configured to heat a liquid composition to generate aerosol and discharge the generated aerosol toward the inserted cigarette such that the generated aerosol passes through the cigarette inserted into the cigarette insertion portion.

BEST MODE

Figure 1A:
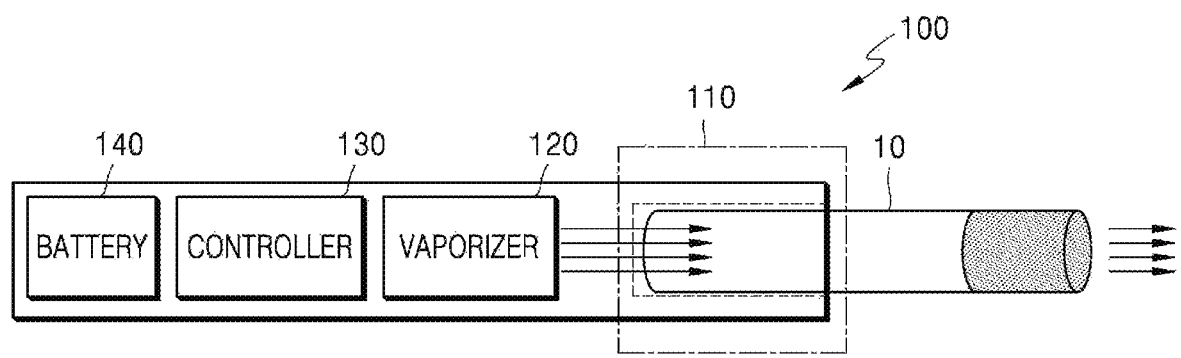
FIGS. 1A and 1B are block diagrams illustrating embodiments of an aerosol generating apparatus.

According to an aspect of the present disclosure, an aerosol generating apparatus includes: a cigarette insertion portion into which a cigarette is insertable; and a vaporizer configured to heat a liquid composition to generate aerosol and discharge the generated aerosol toward the inserted cigarette such that the generated aerosol passes through the cigarette inserted into the cigarette insertion portion.

According to another aspect of the present disclosure, a cradle may include: an inner space capable of receiving an aerosol generating apparatus; a battery configured to supply power to charge the aerosol generating apparatus; and a control unit, wherein the aerosol generating apparatus includes a cigarette insertion portion into which a cigarette is insertable; and a vaporizer configured to heat a liquid composition to generate aerosol and discharge the generated aerosol toward the inserted cigarette such that the generated aerosol passes through the cigarette inserted into the cigarette insertion portion.

Mode of Disclosure

With respect to the terms in the various embodiments of the present disclosure, the general terms which are currently and widely used are selected in consideration of functions of structural elements in the various embodiments of the present disclosure. However, meanings of the terms may be changed according to intention, a judicial precedent, appearance of a new technology, and the like. In addition, in certain cases, a term which is not commonly used may be selected. In such a case, the meaning of the term will be described in detail at the corresponding part in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Throughout the specification, an "aerosol generating material" may mean a material capable of generating aerosol and may mean an aerosol forming substrate. Aerosol may include volatile compounds. The aerosol generating material may be solid or liquid.

For example, the solid aerosol generating material may include a solid material based on a tobacco raw material such as a tobacco sheet, shredded tobacco, reconstituted tobacco, etc. and the liquid aerosol generating material may include a liquid material based on nicotine, tobacco extract and various flavoring agents. The aerosol generating material is not limited to the above examples.

Throughout the specification, an aerosol generating apparatus may be an apparatus that generates aerosol by using an aerosol generating material to generate aerosol capable of being directly inhaled into the user's lung through the user's mouth. For example, the aerosol generating apparatus may be a holder.

Throughout the specification, a "puff" means an inhalation of a user, and the inhalation may mean the drawing of air or other substances into the user's mouth, nasal cavity, or lung through the user's mouth or nose.

Hereinafter, exemplary embodiments of the present disclosure will be described in detail with reference to the accompanying drawings. The disclosure may, however, be embodied in many different forms and should not be construed as limited to the embodiments set forth herein.

Hereinafter, embodiments of the present disclosure will be described in detail with reference to the drawings.

Figure 1B:
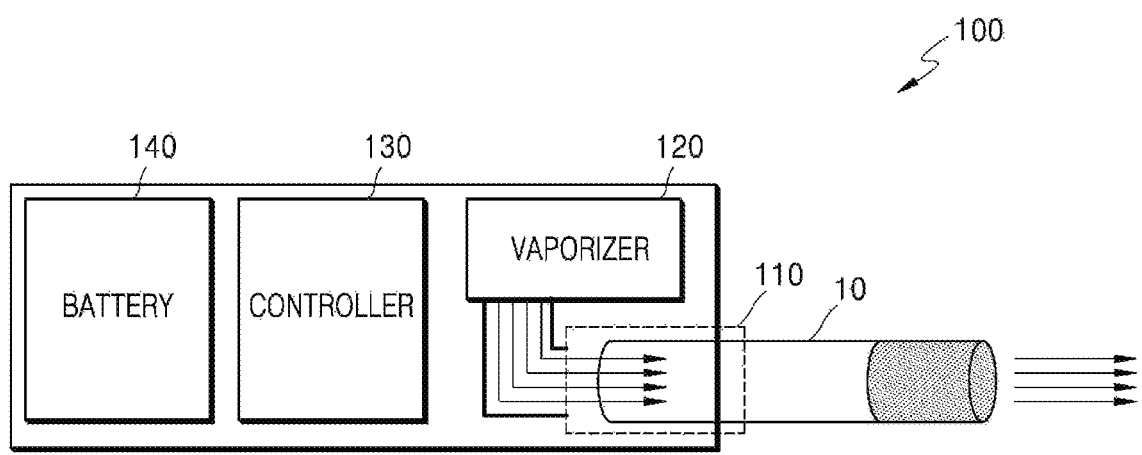

FIGS. 1A and 1B are block diagrams illustrating embodiments of an aerosol generating apparatus.

The aerosol generating apparatus 100 of FIGS. 1A and 1B may include a cigarette inserter 110, a vaporizer 120, a controller 130, and a battery 140. In the aerosol generating apparatus 100 shown in FIGS. 1A and 1B, only components related to the present embodiment are shown. Therefore, it will be understood by those skilled in the art that other general purpose components other than the components shown in FIGS. 1A and 1B may be further included in the aerosol generating apparatus 100. In addition, the aerosol generating apparatus 100 may be in the form of a stick and may be in the form of a holder.

The cigarette inserter 110 corresponds to a region of one end of the aerosol generating apparatus 100, and thus, according to an embodiment, the cigarette inserter 110 may include a space into which a cigarette 10 may be inserted. According to an embodiment, the cigarette 10 may have a shape of a general cigarette, as shown in FIGS. 1A and 1B. According to another embodiment, the cigarette 10 may have a shape in which tobacco raw materials are wrapped in a heat conductive material. For example, the heat conductive material may be a metal foil, such as an aluminum foil.

The vaporizer 120 may heat a liquid composition to generate aerosol and may discharge the generated aerosol through the inserted cigarette 10 such that the generated aerosol passes through the cigarette 10 inserted into the cigarette inserter 110. Therefore, a tobacco flavor may be added to the aerosol that passed through the cigarette 10, and a user may inhale one end of the cigarette 10 by the mouth to inhale the tobacco-flavored aerosol. According to an embodiment, the vaporizer 120 may be referred to as a cartomizer or atomizer.

According to an embodiment, the cigarette inserter 110 may include a heater module for heating the inserted cigarette 10. The heater module may include a tubular heating element, a plate-shaped heating element, a needle- or rod-shaped heating element, and may heat the inside or the outside of the cigarette 10 according to a shape of the heating element. The heater module may heat the cigarette 10 to generate tobacco-flavored aerosol, and accordingly, the user may inhale one end of the cigarette 10 by the mouth and inhale the tobacco-flavored aerosol. Accordingly, the user may inhale the aerosol generated by the vaporizer 120 and the aerosol generated by heating the cigarette 10 together. In addition, the heater module may heat the cigarette 10 at a relatively low temperature (e.g., 40 degrees to 200 degrees).

According to another embodiment, the cigarette inserter 110 may not include the heater module for heating the inserted cigarette 10. In this case, the tobacco flavor may be added to the aerosol generated by the vaporizer 120 even though the aerosol passes through the non-heated cigarette 10. In particular, the taste-controlled cigarette 10 may discharge a tobacco flavor ingredient by a contact with an ambient air or the aerosol. Thus, the user may inhale the tobacco-flavored aerosol from the non-heated cigarette 10. In addition, because of the aerosol generated by heating of the vaporizer 120, the user may inhale aerosol that is relatively warm from the non-heated cigarette 10.

According to an embodiment, the vaporizer 120 may be coupled to the aerosol generating apparatus 100 so as to be replaceable.

The controller 130 controls the overall operation of the aerosol generating apparatus 100. Specifically, the controller 130 controls operations of not only the battery 140 and the vaporizer 120 but also other components included in the aerosol generating apparatus 100. In addition, the controller 130 may check a state of each of the components of the aerosol generating apparatus 100 to determine whether the aerosol generating apparatus 100 is in an operable state.

The controller 130 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

The battery 140 supplies power used to operate the aerosol generating apparatus 100. For example, the battery 140 may supply current to the vaporizer 120 such that the vaporizer 120 may heat the liquid composition. In addition, the battery 140 may supply power necessary for operating a display, a sensor, a motor, etc. installed in the aerosol generating apparatus 100.

The battery 140 may be a lithium iron phosphate (LiFePO4) battery, but is not limited to the example described above. For example, the battery 140 may correspond to a lithium cobalt oxide (LiCoO2) battery, a lithium titantate battery, a lithium ion battery, etc.

The battery 140 may have a cylindrical shape having a diameter of 10 mm and a length of 37 mm, but is not limited thereto. The capacity of the battery 140 may range from 120 mAh to 250 mAh, but is not limited thereto. In addition, the battery 140 may be a rechargeable battery or a disposable battery. For example, when the battery 140 is rechargeable, a charging rate (C-rate) of the battery 140 may be 10 C, a discharging rate (C-rate) may be 10 C to 20 C, but is not limited thereto. In addition, for stable use, the battery 140 may be manufactured such that more than 80% of the total capacity may be secured even when charging/discharging is performed 2000 times.

Meanwhile, the aerosol generating apparatus 100 may further include general purpose components in addition to the battery 140, the controller 130, and the vaporizer 120.

For example, the aerosol generating apparatus 100 may include a display capable of outputting visual information or a motor for outputting tactile information. As an example, when the display is included in the aerosol generating apparatus 100, the controller 130 may transmit information (e.g., whether the vaporizer 120 is available) about a state of the vaporizer 120, information (e.g., a preheating start, a preheating progress, a preheating completion, etc.) about the heater module, information (e.g., remaining capacity of the battery 140, whether the battery 140 is available, etc.) related to the battery 140, information (e.g., a reset time, a reset progress, a reset completion, etc.) related to a reset of the aerosol generating apparatus 100, information (e.g., a cleaning time, necessity of cleaning, a cleaning progress, a cleaning completion, etc.) related to cleaning of the aerosol generating apparatus 100, information (e.g., necessity of charging, a charging progress, a charging completion, etc.) related to charging of the aerosol generating apparatus 100, information (e.g., the strength of the puff etc.) related to a puff of the user, information (e.g. passing of a usage time, etc.) related to safety or the like, to the user through the display. As another example, when the motor is included in the aerosol generating apparatus 100, the controller 130 may generate a vibration signal by using the motor, thereby transmitting the above-described information to the user.

The aerosol generating apparatus 100 may include a terminal coupled with at least one input device (e.g., a button) and/or the cradle 200 through which a user may control the function of the aerosol generating apparatus 100. For example, the user may perform various functions by using the input device of the aerosol generating apparatus 100. By adjusting the number of times (e.g., once or twice) that the user presses the input device or a time (e.g., 0.1 second, 0.2 second, etc.) during which the user is pressing the input device, the user may perform a desired function among a plurality of functions of the aerosol generating apparatus 100. As the user operates the input device, a function of preheating the heating element or the heater module of the vaporizer 120, a function of adjusting a temperature of the heating element or the heater module of the vaporizer 120, a function of cleaning a space in which a cigarette is inserted, a function of checking whether the aerosol generating apparatus 100 is in an operable state, a function of displaying a remaining amount (available power) of the battery 140, a reset function of the aerosol generating apparatus 100, etc. may be performed. However, the function of the aerosol generating apparatus 100 is not limited to the examples described above.

The aerosol generating apparatus 100 may include a puff detection sensor, a temperature detection sensor, and/or a cigarette insertion detection sensor. In addition, the aerosol generating apparatus 100 may be manufactured in a structure in which an external air may be introduced/discharged even when the cigarette is inserted.

According to an embodiment, the aerosol generating apparatus 100 may include the cigarette inserter 110 and the vaporizer 120 arranged in series, as shown in FIG. 1A. According to another embodiment, the aerosol generating apparatus 100 may include the cigarette inserter 110 and the vaporizer 120 arranged in parallel, as shown in FIG. 1B. In addition, an arrangement form of the cigarette inserter 110, the vaporizer 120, the controller 130, and the battery 140 of the aerosol generating apparatus 100 is not limited to FIGS. 1A and 1B, and may vary.

Referring to FIG. 1B, the aerosol generated by the vaporizer 120 may enter the cigarette inserter 110 and pass through the cigarette 10, through an airflow passage in the aerosol generating apparatus 100. Therefore, the tobacco flavor may be added to the aerosol that has passed through the cigarette 10, and the user may inhale one end of the cigarette 10 by the mouth to inhale the tobacco-flavored aerosol.

Figure 2:
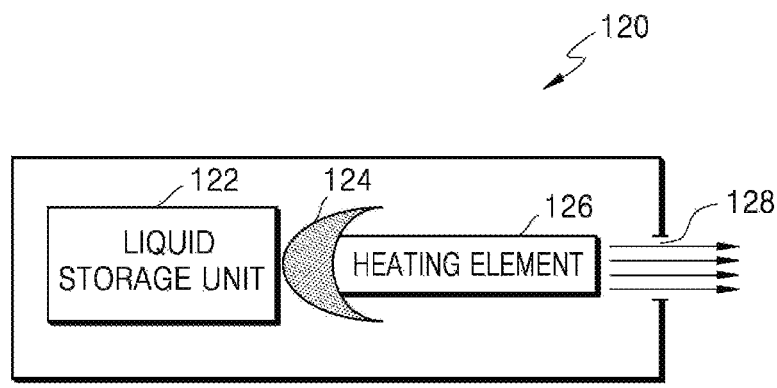
FIG. 2 is a block diagram illustrating an example of a vaporizer.

FIG. 2 is a block diagram illustrating an example of the vaporizer 120.

The vaporizer 120 may include a liquid storage unit 122, liquid transfer means 124, a heating element 126, and an airflow passage 128. Each component of the vaporizer 120 may be made of a material of polycarbonate, but is not limited thereto.

The liquid storage unit 122 may store a liquid composition in which aerosol may be generated when heated. According to an embodiment, the liquid composition may be a liquid including a tobacco containing material including a volatile tobacco aroma ingredient, and according to another embodiment, the liquid composition may be a liquid including a non-tobacco material. In addition, the liquid composition may store 0.1 to 2.0 mL of liquid, but is not limited thereto. In addition, the liquid storage unit 122 may be interchangeably coupled within the vaporizer 120.

For example, the liquid composition may include water, solvents, ethanol, plant extracts, spices, flavor agents, or vitamin mixtures. Spices may include, but is not limited to, menthol, peppermint, spearmint oil, various fruit flavor ingredients, and the like. Flavor agents may include ingredients that may provide a variety of flavors or savors to a user. Vitamin mixtures may be a mixture of at least one of vitamin A, vitamin B, vitamin C and vitamin E, but is not limited thereto. The liquid composition may also include an aerosol former such as glycerin and propylene glycol.

The liquid transfer means 124 may transfer the liquid composition of the liquid storage unit 122 to the heating element 126. According to an embodiment, because the liquid transfer means 124 may be a wick such as a cotton fiber, a ceramic fiber, a glass fiber, and a porous ceramic, the liquid transfer means 124 may transfer the liquid composition of the liquid storage unit 122 to the heating element 126 by using a capillary phenomenon.

The heating element 126 may be an element for heating the liquid composition transferred by the liquid transfer means 124 and may be a metal heating wire, a metal hot plate, a ceramic heater, etc. In addition, the heating element 126 may be composed of a conductive filament such as a nichrome wire, and may be arranged in a structure that is wound around the liquid transfer means 124. The heating element 126 may be heated by a current supply and may transfer heat to the liquid composition in contact with the heating element 126 to heat the liquid composition. As a result, aerosols may be generated.

The airflow passage 128 may be arranged such that the generated aerosol is discharged towards the inserted cigarette 10. That is, the aerosol generated by the heating element 126 may be discharged through the airflow passage 128.

The controller 130 may control the current supplied to the heating element 126 to control a temperature of the heating element 126. Accordingly, the controller 130 may control the current supplied to the heating element 126 to control an amount of aerosol generated from the liquid composition. In addition, the controller 130 may control current to be supplied to the heating element 126 for a preset period of time when a user's puff is sensed. For example, the controller 130 may control the current to be supplied to the heating element 126 for 1 to 5 seconds from when the user's puff is sensed.

The controller 130 may control an open/closed state of the airflow passage 128 to control an amount of aerosol discharged from the vaporizer 120. Specifically, the controller 130 may increase a size of a gap of the airflow passage 128 to increase the amount of the aerosol discharged from the vaporizer 120 and reduce the size of the gap of the airflow passage 128 to reduce the amount of the aerosol discharged from the vaporizer 120. For example, the controller 130 may control the gap of the airflow passage 128 by using a dial method.

When the liquid composition of the liquid storage unit 122 is less than the preset amount, the controller 130 may inform the user that the liquid composition is insufficient, through the vibration motor or the display.

Figure 3:
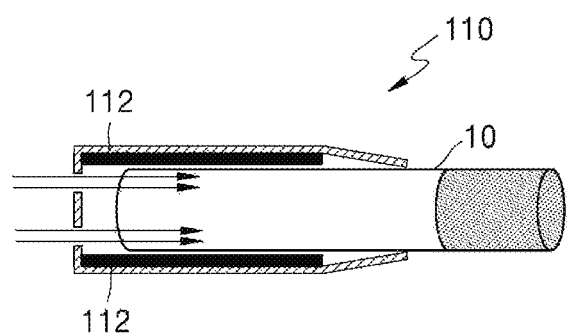
FIG. 3 is a block diagram illustrating an example of a heater module of a cigarette inserter.

FIG. 3 is a block diagram illustrating an example of a heater module 112 of the cigarette inserter 110.

The cigarette inserter 110 may include the heater module 112 for heating an outside of the inserted cigarette 10.

According to an embodiment, the heater module 112 may be configured as a hollow cylinder corresponding to an outer diameter of the cigarette 10 so as to hold the cigarette 10.

The heater module 112 may include a thermally conductive tube, a heater, and a thermal insulator. The thermally conductive tube may be made of an electrically conductive metal. The thermally conductive tube may also be made of ceramic, heat-resistant plastic, or the like, but is not limited thereto. In addition, the thermally conductive tube may have a thickness of 0.1 to 1.0 mm, but is not limited thereto. The heater may be configured as a film heater or a ceramic heater, but is not limited thereto. The thermal insulator may be configured as an aramid material, carbon fiber, glass fiber (silica), or thermal insulating film, but is not limited thereto.

According to an embodiment, the heater module 112 may heat the thermally conductive tube through the heater and heat the cigarette 10 in contact with the thermally conductive tube according to a heat conduction. In addition, according to another embodiment, the heater module 112 may transfer heat through convection and radiation to the cigarette 10 to heat the cigarette 10. Thus, a temperature of an aerosol generating material in the cigarette 10 may increase by heating, and as a result, aerosol may be generated. The generated aerosol may be transferred to a user through a filter of the cigarette 10.

The controller 130 may control the temperature of the heater module 112. Specifically, the controller 130 may control the temperature of the heater module 112 by controlling a pulse width modulation (PWM) or a duty cycle of a current supplied to the heater module 112. In addition, the controller 130 may control a current supply time to control the temperature of the heater module 112. The PWM or the duty cycle of the current supplied to the heater module 112, and the current supply time may be previously set. The controller 130 may control the temperature of the heater module 112 to be maintained constant. For example, the controller 130 may control the temperature of the heater module 112 to be maintained constant at a temperature lower than the temperature of the heater module 112 during preheating.

The controller 130 may control the temperature of the heater module 112, and as a result, may control an amount of aerosol generated by heating of the cigarette 10. Therefore, the controller 130 may control the generation amount of aerosol, thereby controlling the taste intensity that the user may feel by a puff.

Figure 4:
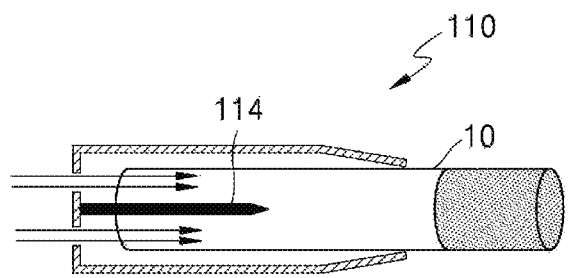
FIG. 4 is a block diagram illustrating another example of a heater module of a cigarette inserter.

FIG. 4 is a block diagram illustrating another example of a heater module 114 of the cigarette inserter 110.

The cigarette inserter 110 may include the heater module 114 for heating an inside of the inserted cigarette 10.

The heater module 114 is heated by power supplied from the battery 140. When the cigarette 10 is inserted into the cigarette inserter 110, the heater module 114 may be located inside the cigarette 10.

The heater module 114 may be configured as a heater in the form of a needle. For example, the heater module 114 may have a cylindrical shape having a diameter of about 2 mm and a length of about 23 mm, and an end of the heater module 114 may be finished at an acute angle, but is not limited thereto. In other words, the heater module 114 may be applied without limitation as long as the heater module 114 may be inserted into the cigarette 10. In addition, only a part of the heater module 114 may be heated. For example, assuming that the length of the heater module 114 is 23 mm, only 12 mm from the end of the heater module 114 may be heated, and the remaining part of the heater module 114 may not be heated.

The heater module 114 may be configured as an electro-resistive heater. For example, the heater module 114 may include an electrically conductive track, and the heater module 114 may be heated as a current flows in the electrically conductive track. The electrically conductive track includes an electro-resistive material. For example, the electrically conductive track may include a metal. In another example, the electrically conductive track may include an electrically conductive ceramic material, a carbon, a metal alloy, or a composite of a ceramic material and a metal.

Thus, a temperature of an aerosol generating material in the cigarette 10 may increase by heating, and as a result, aerosol may be generated. The generated aerosol may be transferred to a user through a filter of the cigarette 10.

Figure 5:
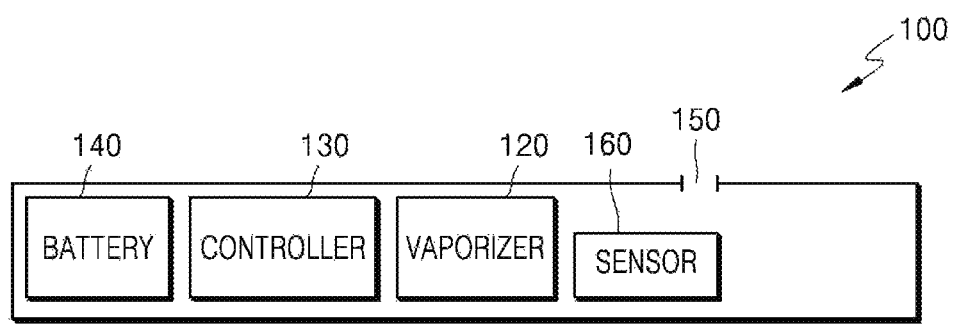
FIG. 5 is a block diagram illustrating another example of an aerosol generating apparatus.

FIG. 5 is a block diagram illustrating another example of the aerosol generating apparatus 100.

The aerosol generating apparatus 100 may further include a sensor 160 and an air inflow passage 150.

The sensor 160 may include at least one of a puff detection sensor, a temperature detection sensor, and a cigarette insertion detection sensor. For example, the puff detection sensor may be implemented by a proximity sensor such as an IR sensor, a pressure sensor, a microphone, a gyro sensor, an acceleration sensor, a magnetic field sensor, or the like. In addition, the cigarette insertion detection sensor may be implemented by a general capacitive sensor or a resistance sensor.

The controller 130 may determine whether a puff of a user occurs based on information sensed by the sensor 160. For example, the sensor 160 may sense a pressure change in the aerosol generating apparatus 100, and the controller 130 may determine that the puff of the user has occurred according to information about the pressure change sensed by the sensor 160. Subsequently, the aerosol generating apparatus 100 may generate aerosol according to the puff of the user. Specifically, the aerosol generating apparatus 100 may generate the aerosol from a liquid composition of a vaporizer or a cigarette. According to another embodiment, the aerosol generating apparatus 100 may generate the aerosol through a separate user input.

The controller 130 may count the number of puffs of the user. In addition, when the number of puffs of the user is greater than or equal to a preset number of times, the controller 130 may forcibly terminate an operation of the aerosol generating apparatus 100 in order to limit the use of the vaporizer 120.

The air inflow passage 150 may be a passage of air introduced from the outside of the aerosol generating apparatus 100. Thus, the aerosol generated from the vaporizer 120 or the cigarette 10 may be mixed with an external air and transferred to the user. In addition, the air inflow passage 150 may include a structure capable of adjusting an air inflow amount. For example, the air inflow passage 150 may include at least one gap and may be manufactured to open or close the at least one gap. Therefore, the controller 130 may control the amount of external air inflow by controlling the opening and closing degree of the at least one gap of the air inflow passage 150, thereby controlling taste, flavor, savor, or the like of tobacco that the user may feel when smoking.

Figure 6:
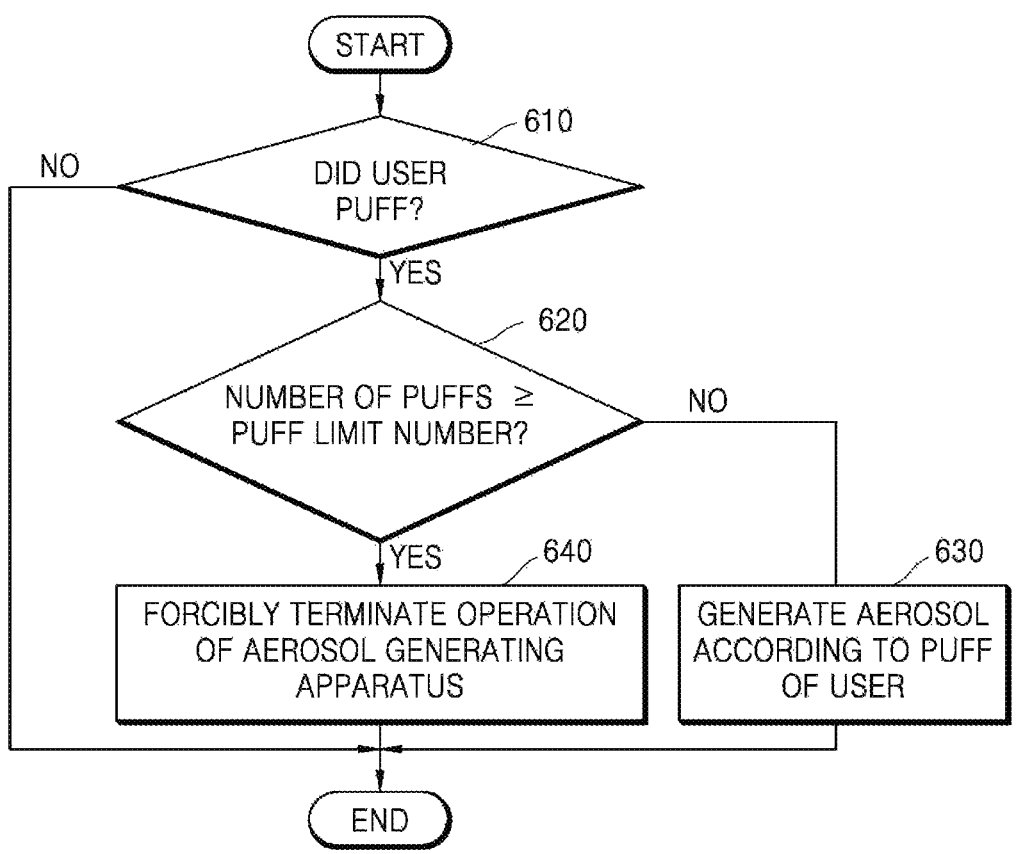
FIG. 6 is a flowchart illustrating an example of operation of an aerosol generating apparatus.

FIG. 6 is a flowchart illustrating an example in which an aerosol generating apparatus operates.

A method of generating aerosol shown in FIG. 6 includes operations processed in time series by the aerosol generating apparatus 100. Therefore, even if omitted below, it may be seen that the above description of the aerosol generating apparatus 100 also applies to a method of FIG. 6.

In operation 610, the aerosol generating apparatus 100 may determine whether a user puffed. For example, the aerosol generating apparatus 100 may determine whether the user puffed through a puff detection sensor.

In operation 620, the aerosol generating apparatus 100 may determine whether the number of puffs of the user is greater than or equal to a puff limit number. Specifically, in operation 610, when a puff of the user occurs, the aerosol generating apparatus 100 may count the number of puffs of the user. For example, when a previous puff is n times, the aerosol generating apparatus 100 may count the number of puffs of the user as n+1 times when the puff of the user has occurred in operation 610. Subsequently, the aerosol generating apparatus 100 may determine whether the counted number of puffs of the user is greater than or equal to a preset puff limit number. According to an embodiment, the preset puff limit number may be determined according to an amount of a liquid composition in a vaporizer. For example, when the liquid composition is 2 mL, the puff limit number may be determined as 200 times. In addition, when the vaporizer or a liquid storage unit in the vaporizer is newly replaced, the aerosol generating apparatus 100 may initialize the number of puffs of the user. For example, the aerosol generating apparatus 100 may initialize the number of puffs of the user to 0.

In addition, when the number of puffs of the user is close to the puff limit number (e.g., when the number of puffs of the user is 180 times), the aerosol generating apparatus 100 may output a warning signal through a display or a vibration motor.

When the number of puffs of the user is greater than or equal to the puff limit number, the aerosol generating apparatus 100 proceeds to operation 640. When the number of puffs of the user is less than the puff limit number, the aerosol generating apparatus 100 proceeds to operation 630.

In operation 630, the aerosol generating apparatus 100 may generate aerosol according to the puff of the user. Specifically, the aerosol generating apparatus 100 may generate the aerosol from the liquid composition of the vaporizer or a cigarette.

In operation 640, the aerosol generating apparatus 100 may forcibly terminate an operation of the aerosol generating apparatus 100. In other words, the aerosol generating apparatus 100 may stop an aerosol generating operation. For example, the aerosol generating apparatus 100 may cut off power supplied to the vaporizer to stop a heating operation of the vaporizer. For another example, the aerosol generating apparatus 100 may cut off power supplied to a heater module to stop a heating operation of the heater module.

Figure 7:
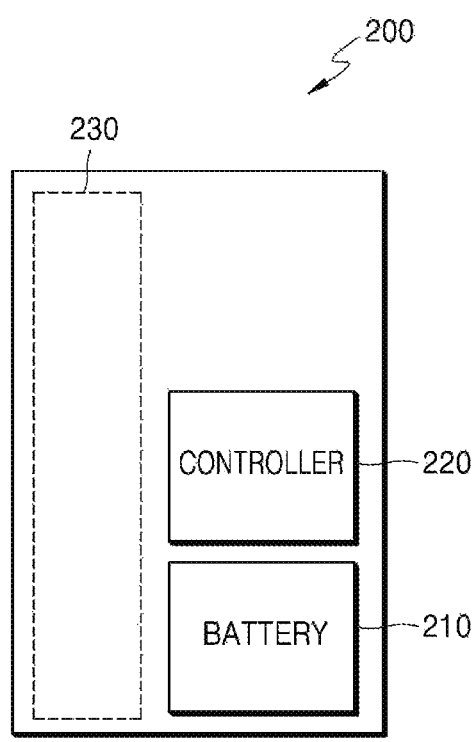
FIG. 7 is a diagram showing an example configuration of a cradle.

FIG. 7 is a diagram showing an example configuration of a cradle.

A cradle 200 includes a battery 210 and a control unit 220. The cradle 2 also includes an inner space 230 into which the aerosol generating apparatus 100 may be inserted.

Only components of the cradle 200 related to the present embodiment are shown in FIG. 7. Therefore, it will be understood by one of ordinary skill in the art that general-purpose components other than the components shown in FIG. 7 may be further included in the cradle 200.

The battery 210 provides power used to operate the cradle 200. In addition, the battery 210 may supply power for charging the battery 140 of which the aerosol generating apparatus 100. For example, when the aerosol generating apparatus 100 is inserted into the cradle 200 and the terminal of the aerosol generating apparatus 100 is coupled with the terminal of the cradle 200, the battery 210 of the cradle 200 may supply power to the battery 140 of the aerosol generating apparatus 100. For example, the battery 210 may supply power to the battery 140 at 2 C to 15 C rate.

Also, when the aerosol generating apparatus 100 is coupled with the cradle 200, the battery 210 may supply power used for the aerosol generating apparatus 100 to operate. For example, when the terminal of the aerosol generating apparatus 100 is coupled with the terminal of the cradle 2, the aerosol generating apparatus 100 may operate by using power supplied by the battery 210 of the cradle 200 regardless of whether the battery 140 of the aerosol generating apparatus 100 is discharged or not. Accordingly, the aerosol generating device 100 may generate an aerosol through the battery 210 of the cradle 200.

An example of the type of the battery 210 may be the same as the example of the battery 140 described above with reference to FIG. 1. The capacity of the battery 210 may be greater than the capacity of the battery 140. For example, the capacity of the battery 210 may be 5 to 40 times the capacity of the battery 140, but is not limited thereto.

The control unit 220 generally controls the overall operation of the cradle 200. The control unit 220 may control the overall operation of all the configurations of the cradle 200. And, the control unit 220 may also determine whether the aerosol generating apparatus 100 is coupled with the cradle 200 and control the operation of the cradle 200 according to coupling or separation of the cradle 200 and the aerosol generating apparatus 100.

For example, when whether the aerosol generating apparatus 100 is coupled with the cradle 200, the control unit 220 may supply power of the battery 210 to the aerosol generating apparatus 100, thereby charging the battery 140.

The control unit 220 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

Meanwhile, the cradle 200 may further include general-purpose components other than the battery 210 and the control unit 220. For example, cradle 200 may include a display capable of outputting visual information. For example, when the cradle 200 includes a display, the control unit 220 generates a signal to be displayed on the display, thereby informing a user information regarding the battery 210 (e.g., the remaining power of the battery 210, availability of the battery 210, etc.), information regarding resetting of the cradle 200 (e.g., reset timing, reset progress, reset completion, etc.), information regarding cleaning of the aerosol generating apparatus 100 (e.g., cleaning timing, cleaning necessity, cleaning progress, cleaning completion, etc.), information regarding charging of the cradle 200 (e.g., charging necessity, charging progress, charging completion, etc.).

And, the cradle 200 may also include at least one input device (e.g., a button) for a user to control the function of the cradle 200, a terminal to be coupled with the aerosol generating apparatus 100, and/or an interface for charging the battery 210 (e.g., an USB port, etc.)

For example, a user may perform various functions by using the input device of the cradle 200. By controlling the number of times that a user presses the input device or a period of time for which the input device is pressed, a desired function from among the plurality of functions of the cradle 200 may be executed. As a user manipulates the input device, the cradle 200 may perform a function of preheating the heater of the aerosol generating apparatus 100 or the vaporizer 120, a function of regulating the temperature of the heater of the aerosol generating apparatus 100 or the vaporizer 120, a function of cleaning the space in which a cigarette is inserted, a function of checking whether the cradle 200 is in an operable state, a function of displaying the remaining power (available power) of the battery 210 of the cradle 200, a function of resetting the cradle 200, etc. However, the functions of the cradle 200 are not limited to the examples described above.

Figure 8A:
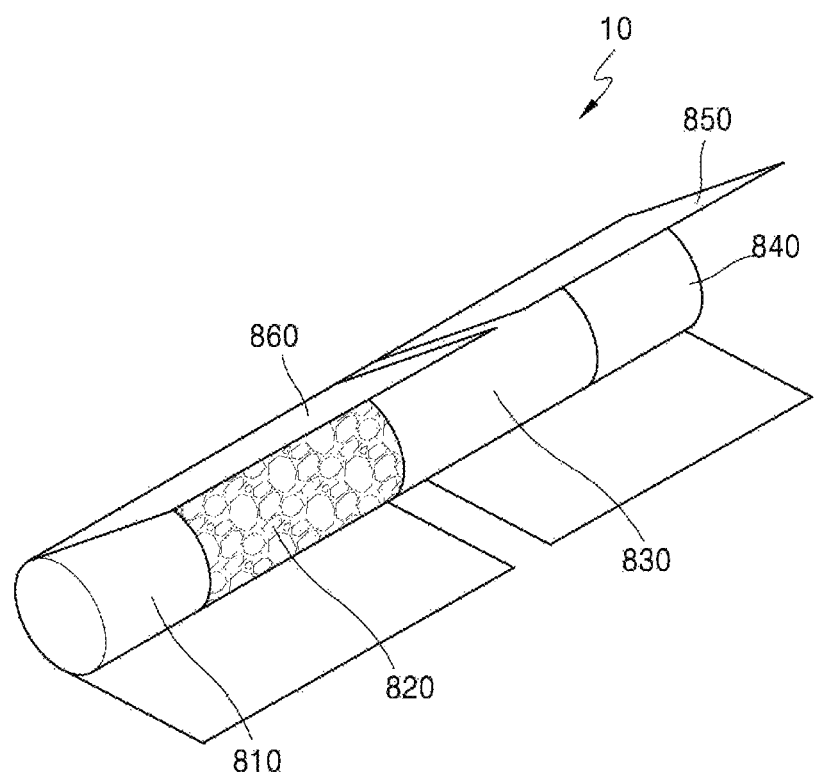
FIGS. 8A and 8B are block diagrams illustrating an example of a cigarette.
Figure 8B:
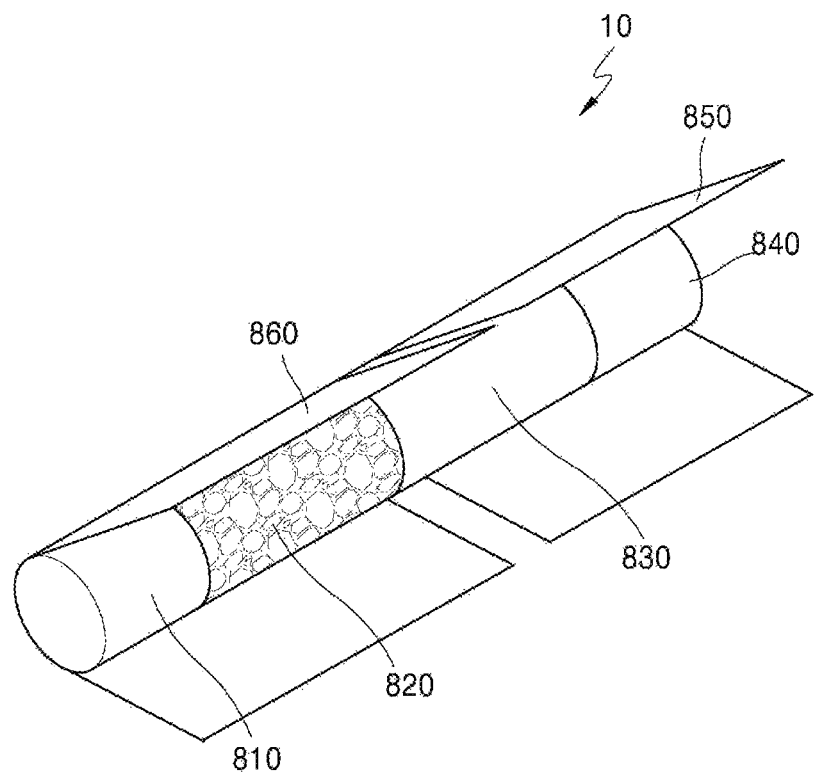

FIGS. 8A and 8B are block diagrams illustrating an example of the cigarette 10.

Referring to FIGS. 8A and 8B, the cigarette 10 may include a first filter segment 810, a tobacco rod 820, a second filter segment 830, a third filter segment 840, and a first wrapper 850.

Meanwhile, upon comparing FIGS. 8A and 8B, the cigarette 10 of FIG. 8B further includes a second wrapper 860 as compared to the cigarette 10 of FIG. 8A.

However, a structure of the cigarette 10 shown in FIGS. 8A and 8B is merely an example, and some configurations may be omitted. For example, the cigarette 10 may not include one or more of the first filter segment 810, the second filter segment 830, and the third filter segment 840.

The first filter segment 810 may be a cellulose acetate filter. In addition, the first filter segment 810 may include a paper filter, porous molding, and the like. For example, a length of the first filter segment 810 may be 4 to 15 mm, but is not limited thereto. In addition, the first filter segment 810 may be colored and may be flavored.

The tobacco rod 820 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol.

The tobacco rod 820 may include a tobacco raw material composed of granules. For example, the size of the granules may be 0.2 to 1.2 mm. In addition, the granules composed of the tobacco raw material may be filled in a cavity of the tobacco rod 820. For example, a filling rate of the tobacco raw material in the tobacco rod 820 may be 30 to 100%. In addition, a filling amount of the tobacco raw material in the tobacco rod 820 may be 0.1 to 2.0 g. According to another embodiment, the tobacco rod 820 may include a tobacco sheet or shredded tobacco composed of a tobacco raw material. The tobacco raw material may be tobacco leaf flakes, tobacco stems, tobacco dust and/or main lateral strips of tobacco leaves generated during tobacco processing.

In addition, the tobacco rod 820 may be taste-controlled. According to an embodiment, in the manufacture of granules or the tobacco sheet of the tobacco rod 820, a taste control agent may be added to the tobacco raw material. In addition, because the tobacco rod 820 may include granules composed of the taste control agent, the tobacco rod 820 may include granules composed of the tobacco raw material and granules composed of the taste control agent. Examples of the taste control agent may include calcium carbonate, sodium bicarbonate, calcium oxide, etc. The taste control agent may control a hydrogen exponent (pH) of the tobacco rod 820 such that the tobacco rod 820 has alkalinity, thereby promoting a flavor ingredient discharge from the tobacco rod 820. Therefore, even in the case where the cigarette 10 is not heated, the same taste expression effect may be produced as in the case where the cigarette 10 is heated.

In addition, the tobacco rod 820 may be flavored. According to an embodiment, in the manufacture of granules or the tobacco sheet of the tobacco rod 820, a flavoring material may be added to the tobacco raw material, and according to another embodiment, the flavoring material may be added to the granules or the tobacco sheet of the tobacco rod 820. The flavoring material may be a material in the liquid state or the solid state. In addition, the flavoring material may be a natural product such as herbal granules and the like, and may be a material such as silica, zeolite, dextrin, etc., including an aroma ingredient.

In addition, the tobacco rod 820 may include other additive materials such as a flavoring agent, a wetting agent, and/or an acetate compound. For example, the flavoring agent may include licorice, sucrose, fructose syrup, iso-sweet, cocoa, lavender, cinnamon, cardamom, celery, fenugreek, cascara, sandalwood, bergamot, geranium, honey essence, rose oil, vanilla, lemon oil, orange oil, mint oil, cinnamon, keragene, cognac, jasmine, chamomile, menthol, cinnamon, ylang ylang, salvia, spearmint, ginger, coriander, coffee, etc. In addition, the wetting agent may include glycerin or propylene glycol.

As an example, the tobacco rod 820 may be filled with shredded tobaccos. Here, shredded tobaccos may be produced by finely pulverizing a tobacco sheet.

In order for a wide tobacco sheet to be filled in the tobacco rod 820 of a small space, a process for easily folding the tobacco sheet is further required. Thus, as compared to filling the tobacco rod 820 with the tobacco sheet, it is easier to fill the tobacco rod 820 with shredded tobaccos, and the productivity and efficiency of a process of producing the tobacco rod 820 may be higher.

As another example, the tobacco rod 820 may be filled with a plurality of tobacco strands in which the tobacco sheet is finely shredded. For example, the tobacco rod 820 may be formed by combining the plurality of tobacco strands with each other in the same direction (in parallel) or randomly. One tobacco strand may be manufactured in a rectangular parallelepiped shape having a horizontal length of 1 mm, a vertical length of 12 mm, and a thickness (height) of 0.1 mm, but is not limited thereto.

Compared to the tobacco rod 820 filled with the tobacco sheet, the tobacco rod 820 filled with the tobacco strands may generate a greater amount of aerosol. Assuming that the tobacco rod 820 is filled in the same space, compared to the tobacco sheet, the tobacco strands ensure a greater surface area. The greater surface area indicates that an aerosol generating material has a greater chance of contacting an external air. Thus, when the tobacco rod 820 is filled with the tobacco strands, more aerosol may be generated compared to when filled with the tobacco sheet. The tobacco sheet may be formed by grinding the tobacco raw material in the form of slurry and then drying the slurry. For example, 15 to 30% of an aerosol generating material may be added to the slurry. The tobacco raw material may be tobacco leaf flakes, tobacco stems, tobacco dust and/or main lateral strips of tobacco leaves generated during tobacco processing. The tobacco sheet may also include other additives such as wood cellulose fibers.

The second filter segment 830 may be configured as a filter including at least one aroma capsule. For example, the second filter segment 830 may be a cellulose acetate filter into which the at least one aroma capsule is inserted. In addition, the second filter segment 830 may be configured as a filter in which flavoring materials are mixed.

The third filter segment 840 may be configured as a tube filter having a hollow therein. For example, the second filter segment 830 may be configured as a cellulose acetate filter or reset filter having the hollow therein.

In addition, at least one of the first filter segment 810, the tobacco rod 820, the second filter segment 830, and the third filter segment 840 may be flavored. Examples of a flavoring method may include a flavoring method in the manufacture of a filter and a method of inserting a thread into the filter.

Also, in the cigarette 10, the first filter segment 810, the tobacco rod 820, the second filter segment 830, and the third filter segment 840 are not limited to an arrangement order as shown in FIG. 8A but may be arranged in various orders. For example, the cigarette 10 may be a cigarette configured in the order as the first filter segment 810, the tobacco rod 820, the third filter segment 840, and the second filter segment 830.

The first wrapper 850 may be made of a general paper packing material. In addition, the first wrapper 850 may be made of paper and film laminate having oil resistance or water resistance. The first filter segment 810, the tobacco rod 820, the second filter segment 830, and the third filter segment 840 may be wrapped by the first wrapper 850.

In addition, a thermally reactive aroma material may be applied to or mixed with the first wrapper 850. Therefore, when the cigarette 10 is heated, aroma may be generated, and the aroma retention may increase.

Referring to FIG. 8B, the cigarette 10 may include a second wrapper 860. At least one of the tobacco rod 820 and the first filter segment 810 may be wrapped by the second wrapper 860. In other words, only the tobacco rod 820 may be wrapped by the second wrapper 860, and the tobacco rod 820 and the first filter segment 810 may be wrapped by the second wrapper 860. For example, the second wrapper 860 may be made of a paper packing material.

The second wrapper 860 may be generated by applying (or coating) a predetermined material to (or on) one surface or both surfaces of the paper packing material. Here, an example of the predetermined material may correspond to, but is not limited to, silicon. Silicon exhibits characteristics like heat resistance with little change due to the temperature, oxidation resistance, resistances to various chemicals, water repellency, electrical insulation, etc. However, any material other than silicon may be applied to (or coated on) the second wrapper 860 without limitation as long as the material exhibits the above-mentioned characteristics.

The second wrapper 860 may prevent the cigarette 10 from being burned. For example, when the tobacco rod 820 is heated, there is a possibility that the cigarette 10 is burned. In detail, when the temperature is raised to a temperature above the ignition point of any one of materials included in the tobacco rod 820, the cigarette 10 may be burned. Even in this case, because the second wrapper 860 includes an uncombustible material, the burning of the cigarette 10 may be prevented. For example, the second wrapper 860 may include the uncombustible material such as aluminum.

Through puffs of a user, liquid substances may be formed in the cigarette 10. For example, aerosol generated by the cigarette 10 is cooled by an external air, and thus liquid materials (e.g., moisture, etc.) may be generated. The second wrapper 860 wraps the tobacco rod 820 and/or the first filter segment 810, the liquid materials generated in the cigarette 10 may be prevented from being leaked out of the cigarette 10.

The embodiments of the present disclosure may be written as computer programs and can be implemented in general-use digital computers that execute the programs using a computer readable recording medium. In addition, the structure of the data used in the above-described method may be recorded on a computer-readable recording medium through various means. Examples of the computer readable recording medium include magnetic storage media (e.g., ROM, RAM, USB drives, floppy disks, hard disks, etc.), optical recording media (e.g., CD-ROMs, or DVDs), etc.

It will be understood by one of ordinary skill in the art that various changes in form and details may be made therein without departing from the spirit and scope of the present disclosure as defined by the appended claims. Therefore, the disclosed methods should be considered from an illustrative point of view, not from a restrictive point of view. The scope of the present disclosure is defined by the appended claims rather than by the foregoing description, and all differences within the scope of equivalents thereof should be construed as being included in the present disclosure.

What is claimed is:

1. An aerosol generating apparatus comprising:
   a vaporizer including a first heater that generates an aerosol by heating a liquid composition, and configured to discharge the generated aerosol; and
   a cigarette inserter configured to receive a cigarette including a plurality of segments, and including a second heater configured to heat a portion of the plurality of segments,
   wherein the generated aerosol is discharged toward the cigarette inserter through an airflow passage arranged between the vaporizer and the cigarette inserter, and passes through the cigarette inserted in the cigarette inserter,
   wherein at least one material vaporized from the heated portion is added to the aerosol which is delivered to a user's mouth through one end of the cigarette,
   wherein the one end of the cigarette is completely exposed out of the cigarette inserter when the cigarette is inserted into the cigarette inserter, and
   wherein the plurality of segments comprise:
      a first filter segment; and
      a tobacco rod comprising a tobacco raw material and disposed downstream of the first filer segment such that the generated aerosol moves from the airflow passage to the tobacco rod through the first filter segment.

2. The aerosol generating apparatus of claim 1, wherein the second heater is further configured to heat an inside of the inserted cigarette.

3. The aerosol generating apparatus of claim 1, wherein the second heater is further configured to heat an outside of the inserted cigarette.

4. The aerosol generating apparatus of claim 1, wherein the second heater is further configured to heat the inserted cigarette according to pulse width modulation (PWM) or a duty cycle of a current supplied from a battery.

5. The aerosol generating apparatus of claim 4, wherein the PWM or the duty cycle of the current is previously set.

6. The aerosol generating apparatus of claim 1, further comprising:
   a sensor configured to detect a puff of a user; and
   a controller configured to determine, through the sensor, whether the puff of the user has occurred.

7. The aerosol generating apparatus of claim 6, wherein the controller is further configured to determine whether a number of puffs of the user is equal to or greater than a preset puff limit number, and according to a result of the determining, determine whether to terminate an operation of the aerosol generating apparatus.

8. The aerosol generating apparatus of claim 6, wherein the controller is further configured to stop a heating operation of the vaporizer when a number of puffs of the user is equal to or greater than a preset puff limit number.

9. The aerosol generating apparatus of claim 1, wherein the vaporizer comprises:
   a liquid storage configured to store the liquid composition; and
   a liquid transfer means for the liquid composition.

10. The aerosol generating apparatus of claim 9, further comprising:
   a controller configured to control a current to be supplied to the first heater for a preset period of time from when a puff of a user is detected.

11. The aerosol generating apparatus of claim 1, wherein the plurality of segments further comprise:
   a third filter segment disposed downstream of the tobacco rod and comprising a hollow; and
   a second filter segment disposed downstream of the third filter segment and comprising at least one aroma capsule.

12. The aerosol generating apparatus of claim 11, wherein the tobacco rod is taste-controlled, and
   wherein at least one of the first filter segment, the tobacco rod, the second filter segment, the third filter segment is flavored.

13. The aerosol generating apparatus of claim 1, further comprising:
   an air inflow passage for air introduced from outside.

14. A cradle comprising:
   an inner space configured to receive an aerosol generating apparatus according to claim 1; and
   a battery configured to supply power to charge the aerosol generating apparatus.

* * * * *